United States Patent
Mochizuki et al.

(10) Patent No.: US 10,117,577 B2
(45) Date of Patent: Nov. 6, 2018

(54) VISUAL FIELD CALCULATION APPARATUS AND METHOD FOR CALCULATING VISUAL FIELD

(71) Applicant: Panasonic Intellectual Property Management Co., Ltd., Osaka (JP)

(72) Inventors: Makoto Mochizuki, Kanagawa (JP); Koichi Emura, Kanagawa (JP); Tetsuo Matsuse, Kanagawa (JP); Hayashi Ito, Kanagawa (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 311 days.

(21) Appl. No.: 14/996,057

(22) Filed: Jan. 14, 2016

(65) Prior Publication Data

US 2016/0120403 A1 May 5, 2016

Related U.S. Application Data

(63) Continuation of application No. PCT/JP2014/003532, filed on Jul. 2, 2014.

(30) Foreign Application Priority Data

Aug. 8, 2013 (JP) .................................. 2013-164963

(51) Int. Cl.
*A61B 3/113* (2006.01)
*A61B 5/00* (2006.01)
(Continued)

(52) U.S. Cl.
CPC ............ *A61B 3/113* (2013.01); *A61B 3/0025* (2013.01); *A61B 3/0041* (2013.01); *A61B 3/024* (2013.01);
(Continued)

(58) Field of Classification Search
CPC ................................ A61B 3/024; A61B 3/113
See application file for complete search history.

(56) References Cited

U.S. PATENT DOCUMENTS

| 5,880,812 A | 3/1999 | Solomon |
| 8,337,019 B2 * | 12/2012 | Murray .................. A61B 3/113 351/208 |
| 2010/0195051 A1 | 8/2010 | Murray et al. |
| 2017/0007119 A1 * | 1/2017 | Cornsweet ............. A61B 3/113 |

FOREIGN PATENT DOCUMENTS

| JP | 2005-095572 | 4/2005 |
| JP | 2011-206072 | 10/2011 |

(Continued)

OTHER PUBLICATIONS

International Search Report of PCT application No. PCT/JP2014/003532 dated Aug. 12, 2014.
(Continued)

*Primary Examiner* — Zachary Wilkes
(74) *Attorney, Agent, or Firm* — Greenblum & Bernstein, P.L.C.

(57) ABSTRACT

A visual field calculation apparatus capable of accurately calculating a visual field range of a user without using a complex configuration is provided. The visual field calculation apparatus includes a saccade detector that detects a saccade on the basis of a first gaze direction detected at a first timing and a second gaze direction detected at a second timing, a saccade speed calculator that calculates speed of the saccade on the basis of a time difference between the first timing and the second timing, the first gaze direction, and the second gaze direction, and a visual field range calculator that calculates a displacement vector of a saccade whose speed exceeds a first threshold, and calculates an area including a final point of the displacement vector as the visual field range of the user.

13 Claims, 20 Drawing Sheets

(51) Int. Cl.
*G02B 27/01* (2006.01)
*A61B 3/024* (2006.01)
*G06K 9/00* (2006.01)
*G08G 1/16* (2006.01)
*A61B 3/00* (2006.01)
*A61B 5/0496* (2006.01)
*G06F 3/01* (2006.01)

(52) U.S. Cl.
CPC ............ *A61B 5/6893* (2013.01); *G02B 27/01* (2013.01); *G02B 27/0101* (2013.01); *G06K 9/00604* (2013.01); *G08G 1/162* (2013.01); *G08G 1/166* (2013.01); *A61B 5/0496* (2013.01); *G02B 2027/0123* (2013.01); *G02B 2027/0187* (2013.01); *G06F 3/01* (2013.01)

(56) References Cited

FOREIGN PATENT DOCUMENTS

| WO | 1998/040781 | 9/1998 |
| WO | 2008/139137 | 11/2008 |

OTHER PUBLICATIONS

Extended European Search Report from European Patent Office (EPO) dated Jun. 30, 2016 for the related European Patent Application No. 14834591.1.

\* cited by examiner

FIG. 5

| SACCADE DISPLACEMENT | THRESHOLD |
|---|---|
| 0° OR WIDER BUT NARROWER THAN 10° | 150°/sec |
| 10° OR WIDER BUT NARROWER THAN 20° | 200°/sec |
| 20° OR WIDER BUT NARROWER THAN 30° | 300°/sec |

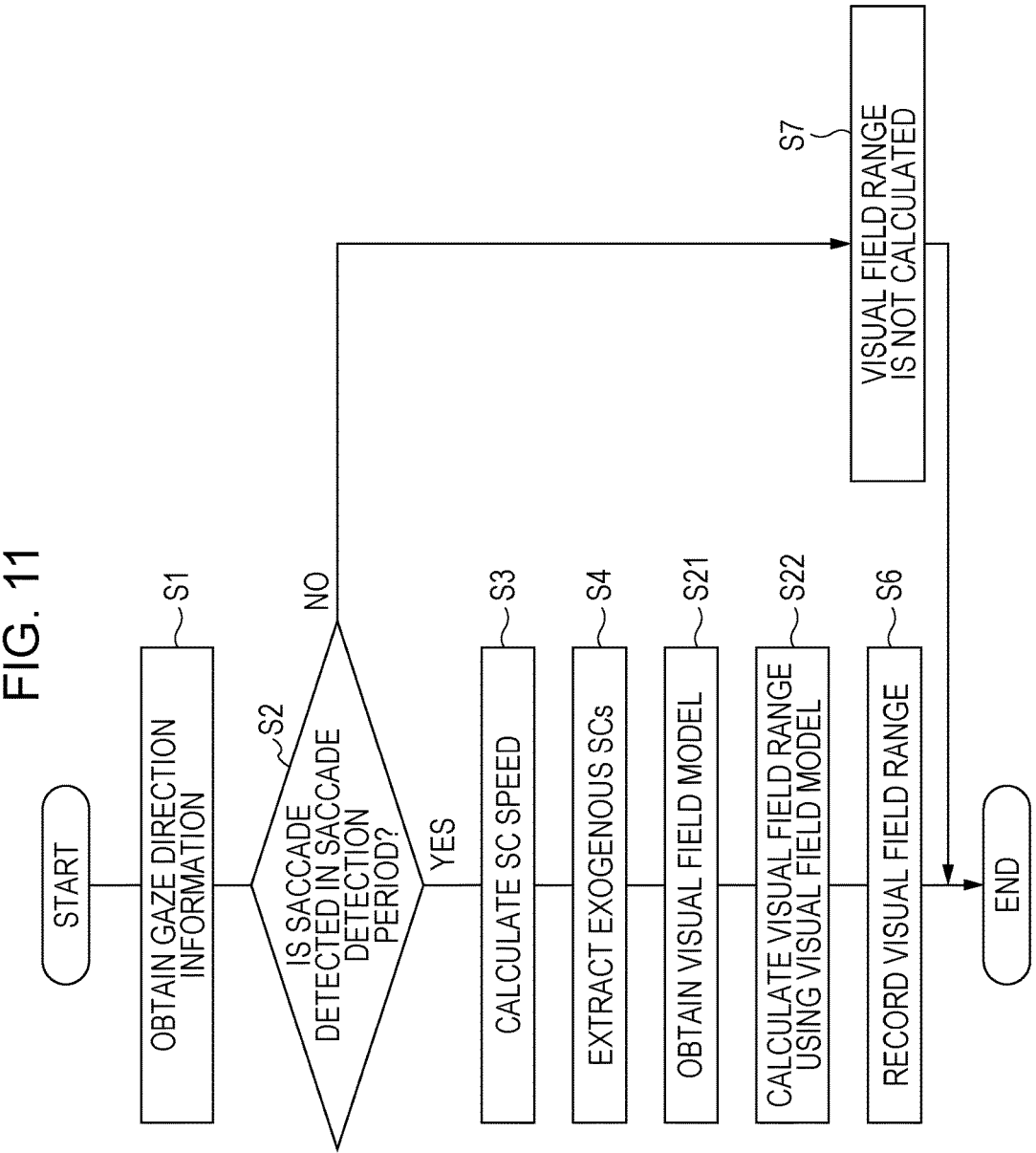

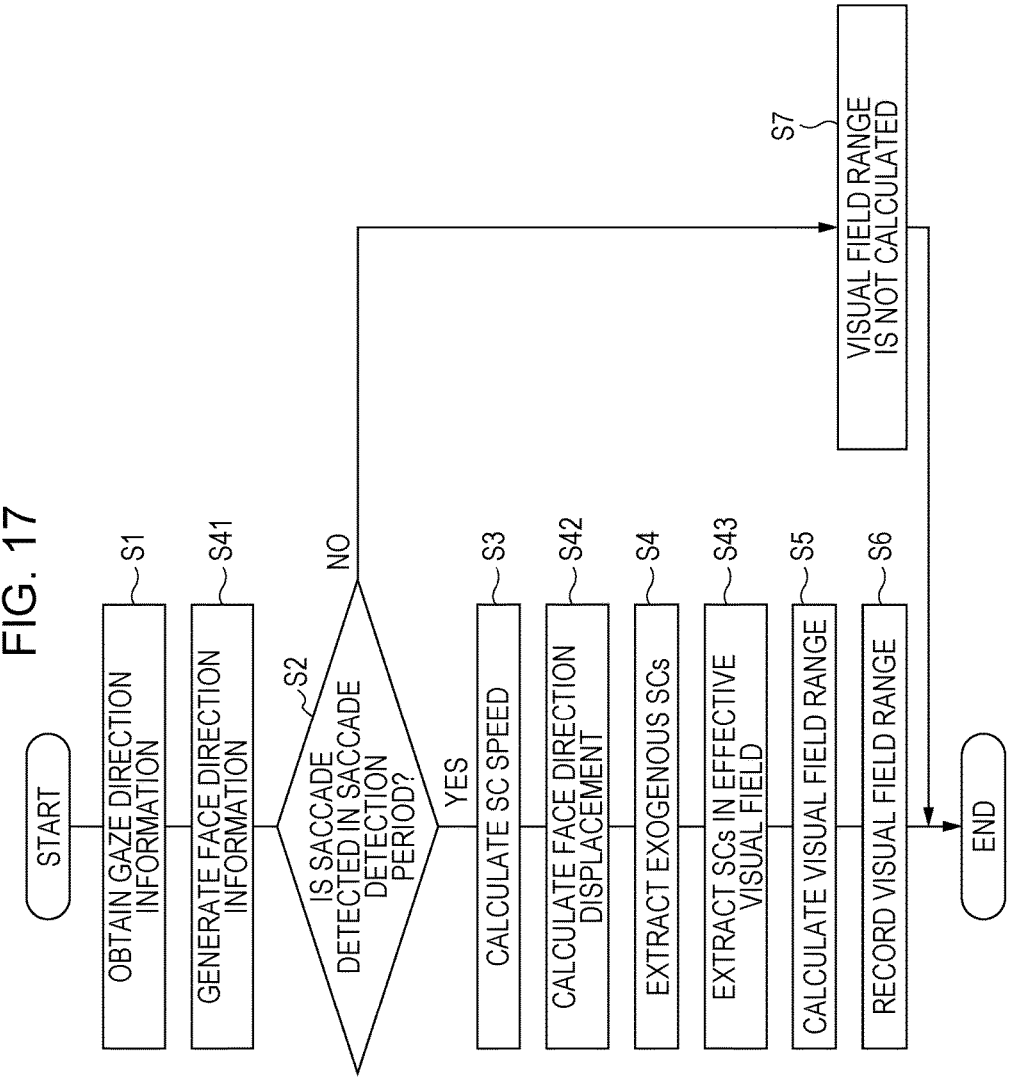

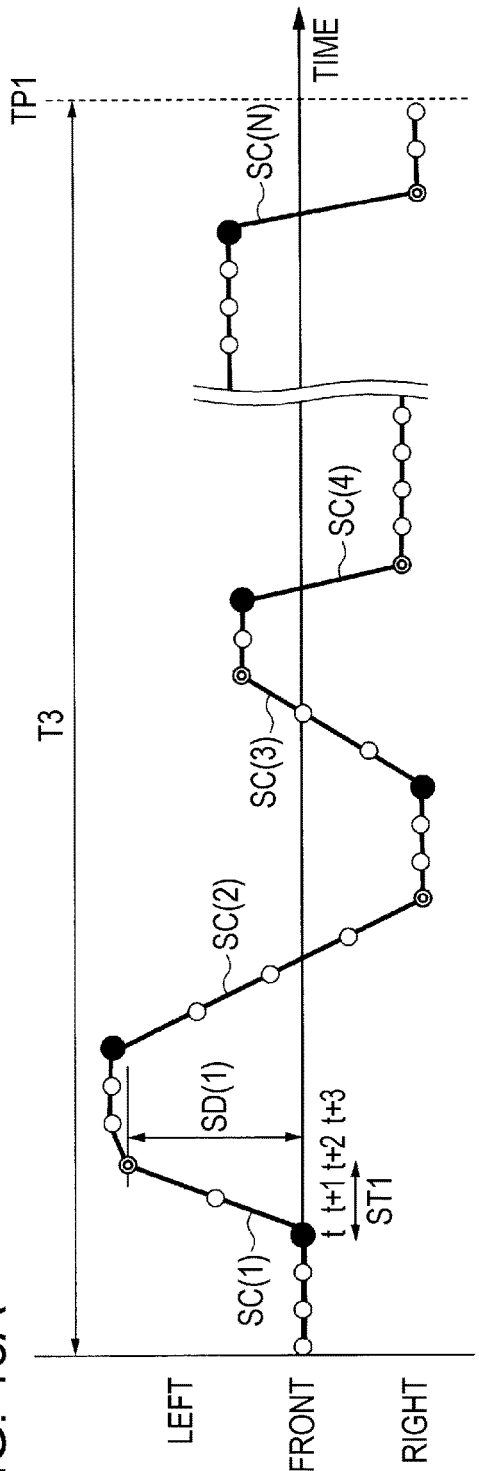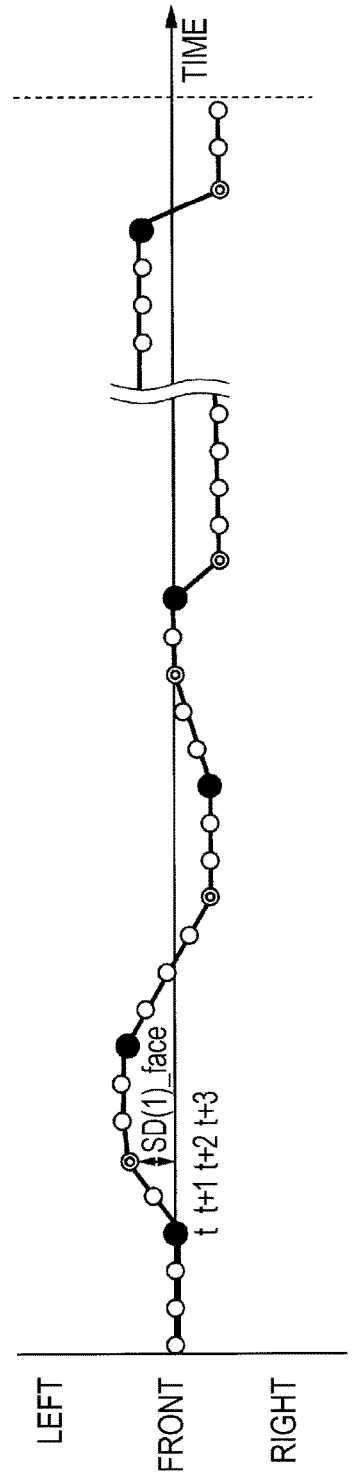
FIG. 18A
FIG. 18B

VISUAL FIELD CALCULATION APPARATUS AND METHOD FOR CALCULATING VISUAL FIELD

BACKGROUND

1. Technical Field

The present disclosure relates to a visual field calculation apparatus and a method for calculating a visual field.

2. Description of the Related Art

As a method for calculating a visual field range (also referred to as a "visual field area") of a user who is driving a vehicle, a method disclosed in Japanese Unexamined Patent Application Publication No. 2011-206072, for example, is currently known. In the method described in Japanese Unexamined Patent Application Publication No. 2011-206072, a moving object (e.g., a person) outside a vehicle is detected using means for detecting a moving object outside the vehicle, and a gaze direction of the user is measured using means for detecting a gaze direction of the user. If it is determined on the basis of the moving object and the gaze direction that the user is gazing at a moving object outside the vehicle, the visual field range is calculated on the basis of the position of a gaze point.

SUMMARY

In the method of Japanese Unexamined Patent Application Publication No. 2011-206072, however, means (e.g., a device such as a camera) for detecting a moving object outside the vehicle needs to be included in addition to means for detecting the gaze direction of the user, which makes configuration complex.

One non-limiting and exemplary embodiment provides a visual field calculation apparatus whose configuration is simpler and that can calculate the visual field range.

In one general aspect, the techniques disclosed here feature a visual field calculation apparatus according to an aspect of the present disclosure is a visual field calculation apparatus that calculates a visual field range of a user on the basis of a detected gaze direction of the user. The visual field calculation apparatus includes a saccade detection unit that detects a saccade on the basis of a first gaze direction detected at a first timing and a second gaze direction detected at a second timing, a saccade speed calculation unit that calculates speed of the saccade on the basis of a time difference between the first timing and the second timing, the first gaze direction, and the second gaze direction, and a visual field range calculation unit that calculates a displacement vector of a saccade whose speed exceeds a first threshold, and calculates an area including an initial point and a final point of the displacement vector as the visual field range of the user.

According to the visual field calculation apparatus according to the present disclosure, the visual field range can be calculated with a simpler configuration.

It should be noted that general or specific embodiments may be implemented as a system, a method, an integrated circuit, a computer program, a storage medium, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 5 is a diagram illustrating an example of saccade speed thresholds according to the first embodiment of the present disclosure;

FIG. 11 is a flowchart illustrating an example of an operation for calculating the visual field according to the modification of the first embodiment of the present disclosure;

FIG. 17 is a flowchart illustrating an example of an operation for calculating the visual field according to the third embodiment of the present disclosure;

FIGS. 18A and 18B are conceptual diagrams illustrating an example of a process for detecting a saccade and a process for calculating a face displacement according to the third embodiment of the present disclosure;

DETAILED DESCRIPTION

Figure 1:
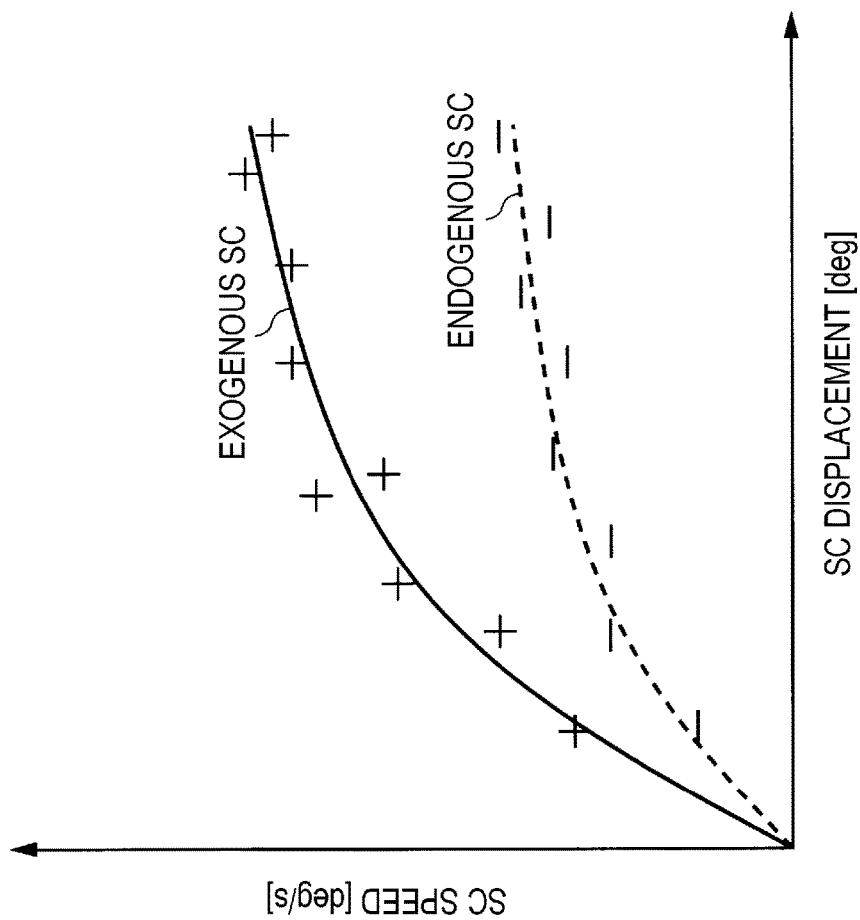
FIG. 1 is a graph illustrating properties of an exogenous saccade and an endogenous saccade.

Calculation of Visual Field Range Using Provision of Targets

First, a general example of calculation of a visual field range will be described. A method in which provision of targets is used, for example, has been disclosed in "TR S 0004 2010: Data on the Age-related Changes of Visual Field Size for Detection", issued by the Japanese Standards Association on Apr. 1, 2010. In the method described in "TR S 0004 2010: Data on the Age-related Changes of Visual Field Size for Detection" (hereinafter also referred to as a method of "TR S 0004 2010: Data on the Age-related Changes of Visual Field Size for Detection"), targets are displayed on a screen provided in front of a user. Reactions of the user to the targets are measured in order to calculate the visual field range.

The method will be specifically described hereinafter. In the method of "TR S 0004 2010: Data on the Age-related Changes of Visual Field Size for Detection", targets are displayed on the screen in front of the user in eight directions, namely upward, downward, left, right, upper right, upper left, lower left, and lower right of an origin, which is a point directly in front of the user, at an eccentric angle of 10 to 60 degrees for 200 msec. In the method of "TR S 0004 2010: Data on the Age-related Changes of Visual Field Size for Detection", the visual field range is then calculated on the basis of a result of a determination as to whether the user was able to recognize each target while gazing at the center of the screen. The visual field range herein is defined as a "visual field in which existence of an object can be detected". More specifically, the visual field range is a range in which the user can notice existence of an object when the object appears around the user's gaze while the user is gazing forward. The visual field range is defined as a "detection visual field" in "TR S 0004 2010: Data on the Age-related Changes of Visual Field Size for Detection".

In general, the visual field range changes depending on various factors such as the user's age or state (e.g., a psychological state or vigilance), the complexity of a foreground, and the user's action. Because the method of "TR S 0004 2010: Data on the Age-related Changes of Visual Field Size for Detection" is implemented in order to collect basic data regarding the visual field range of young and elderly people in an experiment environment, calculation of the visual field range in a case, such as during driving of a vehicle, where the visual field range changes depending on the situation is not assumed. That is, it is difficult to use the method of "TR S 0004 2010: Data on the Age-related Changes of Visual Field Size for Detection", which needs components such as a screen and targets, to calculate the visual field range during driving.

Principle Used for Calculating Visual Field Range

A principle used for calculating the visual field range (hereinafter also referred to as "visual field calculation" as necessary) in embodiments of the present disclosure that will be described later will be described.

When the user takes some action typified by driving of an automobile, an eye movement usually occurs in order to obtain a surrounding environment. In the case of driving of an automobile, it is said that a driver obtains approximately 90% of information necessary for the driving from visual information, and the driver sequentially switches a target at which he/she gazes. Such an eye movement that occurs when the driver switches the target at which he/she gazes is called a "saccade" (hereinafter referred to as an "SC" as necessary). The displacement of a saccade is 0.5 degree to 50 degrees, and the speed of a saccade is 100 to 500 degrees per second. That is, a saccade refers to a very high speed eye movement.

SCs are divided into exogenous SCs and endogenous SCs in accordance with different occurrence factors. Exogenous SCs are also referred to as "externally triggered SCs", which are substantially reflexively caused SCs due to visual stimuli that suddenly appear in the visual field. On the other hand, endogenous SCs are also referred to as "internally guided SCs", which are deliberately caused from motives inside of the user. In addition, endogenous SCs are considered irrelevant to the visual field range.

Various studies have been conducted on properties of exogenous SCs and endogenous SCs. As a result, in "Analysis of Dynamic Properties of Saccades Occurring during Smooth Pursuit Eye Movement", Institute of Electronics, Information and Communication Engineers Journal Vol. J78-D-II No. 5 pp. 845-854, Characteristics of Visually Triggered and Internally Guided Saccade Depending on Vigilance States, it has been found that the highest speed of exogenous SCs is higher than that of endogenous SCs and the distribution of highest speeds differs between exogenous SCs and endogenous SCs in accordance with the displacement of the SCs.

FIG. 1 is a graph illustrating the properties of exogenous SCs and endogenous SCs. In FIG. 1, a vertical axis represents SC speed (degrees/second), and a horizontal axis represents SC displacement (degrees). The exogenous SCs are indicated by "+", and the endogenous SCs are indicated by "−". In addition, in FIG. 1, an approximate curve of the distribution of the exogenous SCs is indicated by a solid line, and an approximate curve of the distribution of the endogenous SCs is indicated by a broken line. As can be seen from FIG. 1, by providing a threshold for the SC speed in accordance with the SC displacement, exogenous SCs and endogenous SCs can be separated from each other.

The embodiments of the present disclosure that will be described later use the above principle to exclude endogenous SCs, which are irrelevant to the visual field range, and extract only exogenous SCs, which are reactions to visual stimuli in the visual field, thereby making it possible to calculate the visual field range of the user accurately.

First to fourth embodiments of the present disclosure will be described hereinafter with reference to the drawings.

First Embodiment

The first embodiment of the present disclosure will be described.

Figure 2:
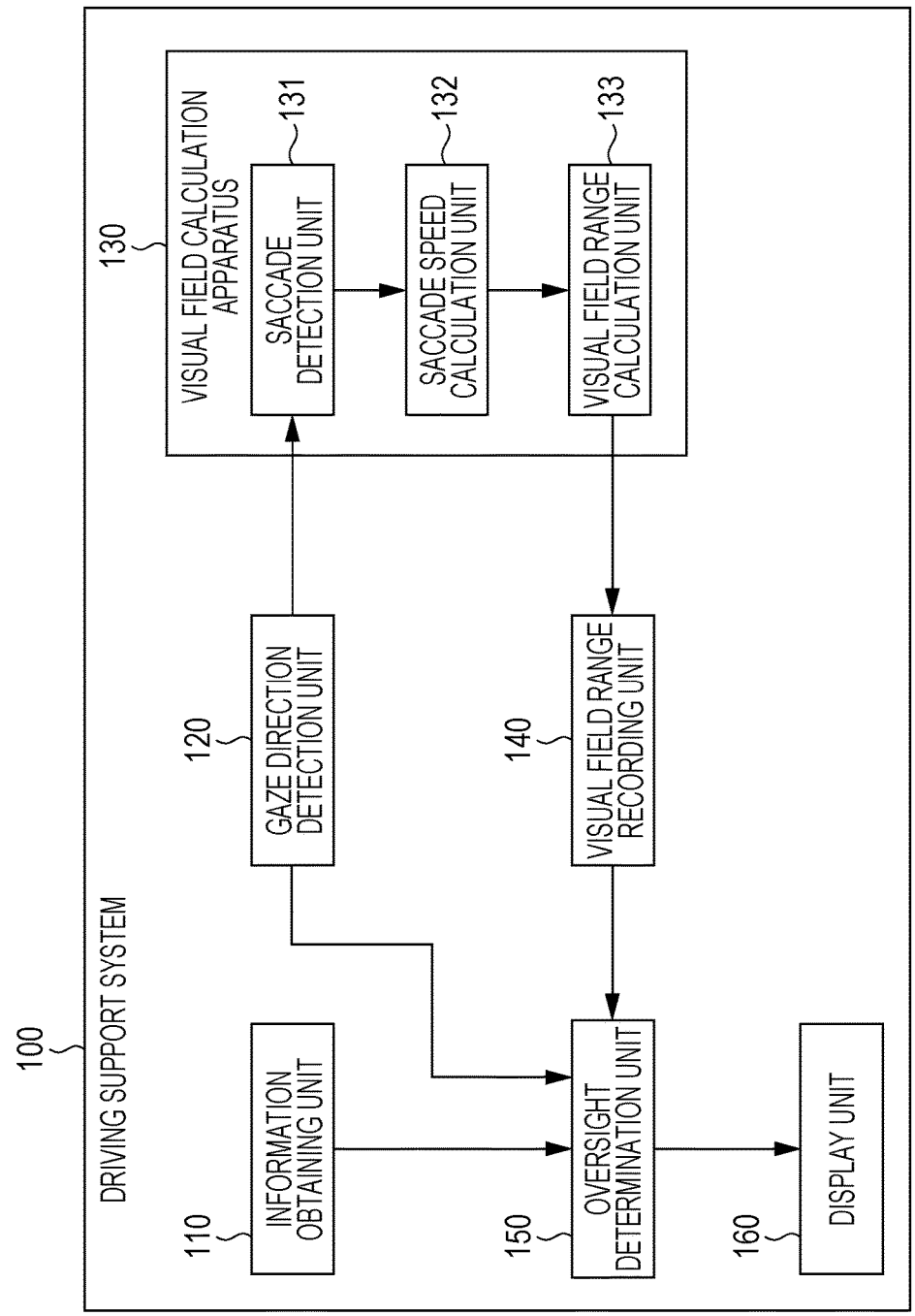
FIG. 2 is a block diagram illustrating an example of the configuration of a driving support system and a visual field calculation apparatus according to a first embodiment of the present disclosure.

FIG. 2 is a block diagram illustrating an example of the configuration of a driving support system 100 including a visual field calculation apparatus 130 according to the present embodiment. In FIG. 2, the driving support system 100 includes an information obtaining unit 110, a gaze direction detection unit 120, the visual field calculation apparatus 130, a visual field range recording unit 140, an oversight determination unit 150, and a display unit 160.

The driving support system 100 is a system that is mounted on a vehicle such as an automobile, detects an obstacle around the vehicle missed by the user, and issues an alarm, a warning, or the like to the user using at least either auditory means or visual means. As a result, it is possible to prevent the user from missing an obstacle around the vehicle and support safe driving. It is to be noted that the "user" in the first to fourth embodiments refers to a driver of a vehicle on which the driving support system 100 is mounted.

The information obtaining unit 110 obtains obstacle information. The obstacle information is information including presence or absence of an obstacle around the vehicle, the position of the obstacle, the speed of the obstacle relative to the vehicle, and the like. The obstacle information is obtained using a vehicle sensor such as a camera or a millimeter wave radar mounted on the vehicle, a sensor mounted on a road, wireless communication, and the like. In addition, obstacle information obtained by another vehicle may be obtained through inter-vehicle communication.

The gaze direction detection unit 120 detects a gaze direction of the user (hereinafter referred to as a "gaze direction" as necessary). The gaze direction detection unit 120 calculates, using a corneal reflex method or the like, for example, an eye movement from an image obtained using a camera that captures an image of an eyeball of the user. The corneal reflex method is a method in which a near-infrared light source (point-source light) radiates near-infrared light onto an eyeball, a camera captures an image of the eyeball, and the position of a pupil and the position of a corneal reflex image of the light source on a surface of a cornea are detected using the captured image. The gaze direction detection unit 120 detects the gaze direction of the user on the basis of a calculated positional relationship between the pupil and the corneal reflex image. The gaze direction refers to a direction in which the user gazes. The gaze direction is expressed by an angle in a horizontal direction and an angle in a vertical direction (unit: degrees) relative to a forward direction of the vehicle. It is to be noted that the gaze direction detection unit 120 may be, for example, an apparatus provided around a steering column of a driver's seat or a head-mounted measuring device worn by the user.

The visual field calculation apparatus 130 calculates the visual field range of the user on the basis of the gaze direction of the user detected by the gaze direction detection unit 120. The visual field calculation apparatus 130 includes a saccade detection unit 131, a saccade speed calculation unit 132, and a visual field range calculation unit 133.

The saccade detection unit 131 obtains the gaze direction of the user detected by the X-ray generation apparatus 102 in chronological order and detects presence or absence of a saccade on the basis of the gaze direction.

The saccade speed calculation unit 132 calculates the saccade speed (SC speed) for a saccade detected by the saccade detection unit 131 on the basis of the saccade displacement (SC displacement) and the duration of the saccade.

The visual field range calculation unit 133 calculates the visual field range of the user using only saccades whose saccade speeds calculated by the saccade speed calculation unit 132 are higher than a certain threshold. Details of the calculation will be described later. As described with reference to FIG. 1, the threshold is a value with which exogenous SCs and endogenous SCs can be separated from each other.

The visual field range recording unit 140 records the visual field range of the user calculated by the visual field calculation apparatus 130.

The oversight determination unit 150 determines whether the user is missing an obstacle on the basis of the obstacle information obtained by the information obtaining unit 110, the gaze direction of the user calculated by the gaze direction detection unit 120, and the visual field range of the user recorded by the visual field range recording unit 140.

The display unit 160 provides information indicating a missed obstacle determined by the oversight determination unit 150 for the user. The display unit 160 may display an icon or the like indicating an obstacle on a display apparatus such as a car navigation apparatus, or may output an alarm sound or a warning along with the displayed icon.

Next, an operation for calculating the visual field and an operation for determining an oversight will be described in this order as examples of the operation of the driving support system 100.

Operation for Calculating Visual Field

Figure 3:
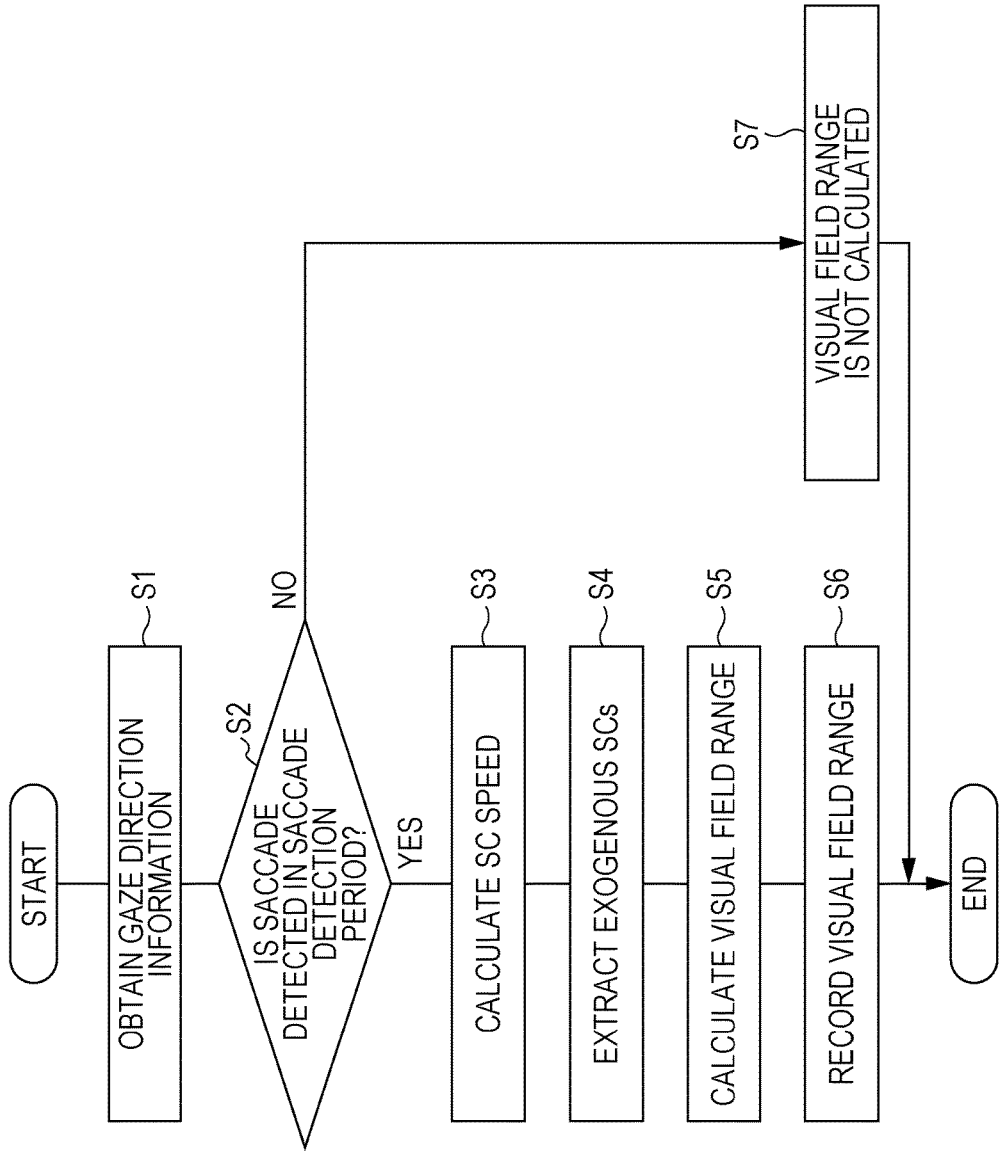
FIG. 3 is a flowchart illustrating an example of an operation for calculating a visual field according to the first embodiment of the present disclosure.

First, an example of the operation for calculating the visual field will be described with reference to a flowchart of FIG. 3. The operation for calculating the visual field is performed by the visual field calculation apparatus 130. In addition, it is assumed that the operation for calculating the visual field is performed independently of the operation for determining an oversight, which will be described later, at certain time intervals T1 such as, for example, 10 minutes, 30 minutes, or 60 minutes.

In step S1, the saccade detection unit 131 obtains gaze direction information from the gaze direction detection unit 120 and records the gaze direction of the user indicated by the information as the gaze direction for a certain period. The gaze direction information is information indicating the gaze direction of the user detected by the gaze direction detection unit 120.

In step S2, the saccade detection unit 131 detects a saccade in a saccade detection period T3 using gaze direction information obtained between a visual field calculation operation start point (TP1 illustrated in FIG. 4) and a point in time a certain period of time before the visual field calculation operation start point (hereinafter referred to as a "saccade detection period"; T3 illustrated in FIG. 4). If a saccade is detected (YES in step S2), a flow proceeds to step S3. On the other hand, if a saccade is not detected (NO in step S2), the flow proceeds to step S7.

Figure 4:
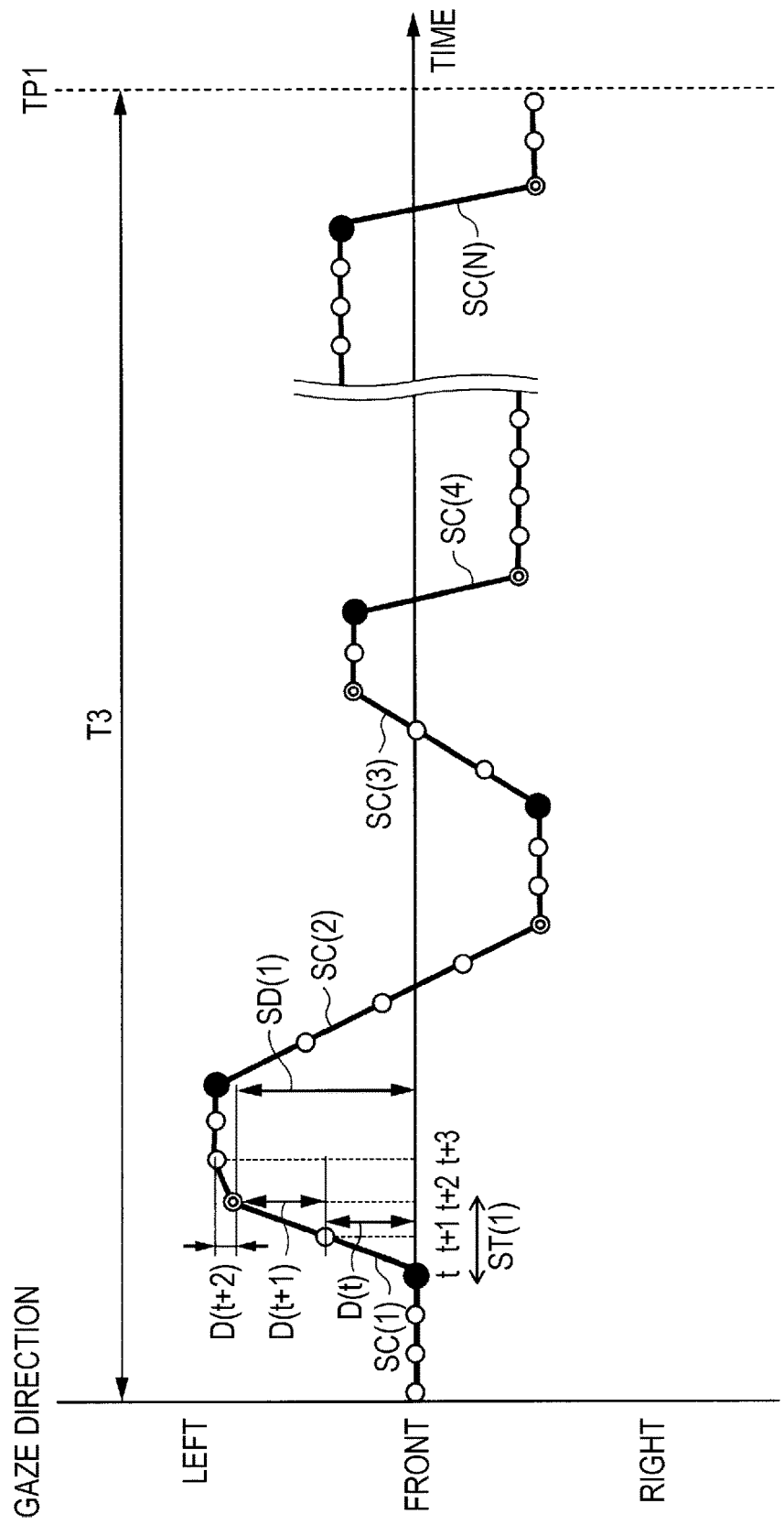
FIG. 4 is a conceptual diagram illustrating an example of a process for detecting a saccade according to the first embodiment of the present disclosure.

Now, a process for detecting a saccade performed in step S2 will be described with reference to FIG. 4. In FIG. 4, a vertical axis represents the gaze direction (unit: degrees) of the user, and a horizontal axis represents time (t). Temporal changes in the gaze direction of the user in the saccade detection period T3 are schematically illustrated. The gaze direction of the user represented by the vertical axis illustrated in FIG. 4 is, for example, an angle of a horizontal direction component (left and right). Detection of a saccade based on the horizontal direction component, therefore, will be described hereinafter. It is to be noted that although description is omitted, detection of a saccade based on a vertical direction component (upward and downward) is performed using the same method as described below.

A saccade is a very high speed eye movement whose speed is 100 to 500° per second. The saccade detection unit 131 detects a saccade on the basis of the amount of movement of the gaze direction in unit time.

First, if a difference between a horizontal angle in the gaze direction at a time T and a horizontal angle in the gaze direction at a time T+1 is denoted by D(T), the saccade detection unit 131 calculates D(T) at each point in time. In FIG. 4, t is an example of T, t+1 is an example of T+1, and D(t) is an example of D(T).

Next, the saccade detection unit 131 detects a point in time when D(T) exceeds a threshold D_th (an example of a first threshold) as a saccade start point Ts. The saccade start point Ts is indicated by a solid circle in FIG. 4. In addition, in FIG. 4, t is an example of Ts.

Next, the saccade detection unit 131 detects a point in time when D(T) falls below the threshold D_th as a saccade end time Te. The saccade end time Te is indicated by a double circle in FIG. 4. In addition, in FIG. 4, t+2 is an example of Te.

The saccade detection unit 131 then detects the points Ts to Te as a saccade period ST and D(Ts)+D(Ts+1)+ . . . +D(Te−1) as a saccade displacement SD. In FIG. 4, t to t+1 is an example of ST, and D(t)+D(t+1) is an example of SD.

The saccade detection unit 131 thus detects, in the saccade detection period T3, a saccade SC(1) to a saccade SC(N) (N is a positive integer; the same holds in the following description) and saccade periods ST(1) to ST(N) and saccade displacements SD(1) to SD(N) corresponding to these saccades. It is to be noted that, in FIG. 4, illustration of saccade periods ST and saccade displacements SD is omitted for the saccades SC(2) to SC(N).

In step S3, the saccade speed calculation unit 132 calculates a saccade speed SV(i) on the basis of a detected saccade period ST(i) and a detected saccade displacement SD(i). The saccade speed calculation unit 132 calculates SD(i)/ST(i), for example, and SV(i).

In step S4, the visual field range calculation unit 133 extracts saccades whose saccade speeds are higher than the certain threshold from among the detected saccades. As described above, the threshold is a value with which exogenous SCs and endogenous SCs can be separated from each other. The extracted saccades are, therefore, exogenous SCs. As can be seen from the properties of exogenous SCs and endogenous SCs illustrated in FIG. 1, in order to separate exogenous SCs and endogenous SCs from each other accurately, a larger threshold is desirably used as the SC displacement increases. As illustrated in FIG. 5, for example, the threshold may be changed in accordance with the saccade displacement SD.

In step S5, the visual field range calculation unit 133 calculates, for an extracted exogenous SC, a vector (hereinafter referred to as an "exogenous SC vector") whose initial point is at coordinates at a saccade start point and whose final point is at coordinates at a saccade end point. The visual field range calculation unit 133 then calculates an area calculated from a plurality of exogenous SC vectors as the visual field range. The above-described coordinates at a saccade start point and the coordinates at a saccade end point are both coordinates obtained on the basis of the gaze direction (the angle of the horizontal direction component and the angle of the vertical direction component) of the user.

Figure 6A:
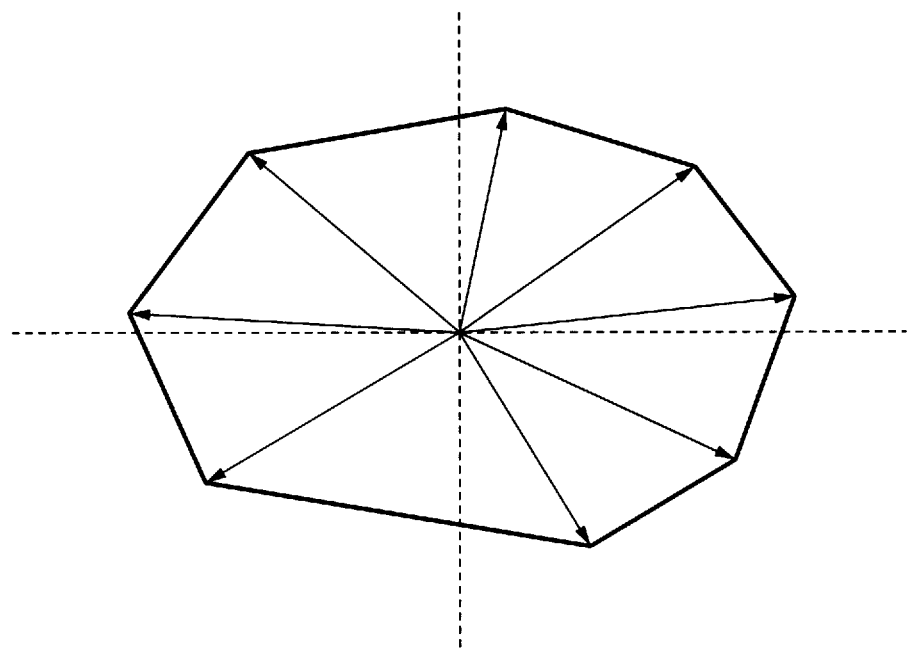
FIGS. 6A and 6B are conceptual diagrams illustrating examples of the visual field calculated by the visual field calculation apparatus according to the first embodiment of the present disclosure.
Figure 6B:
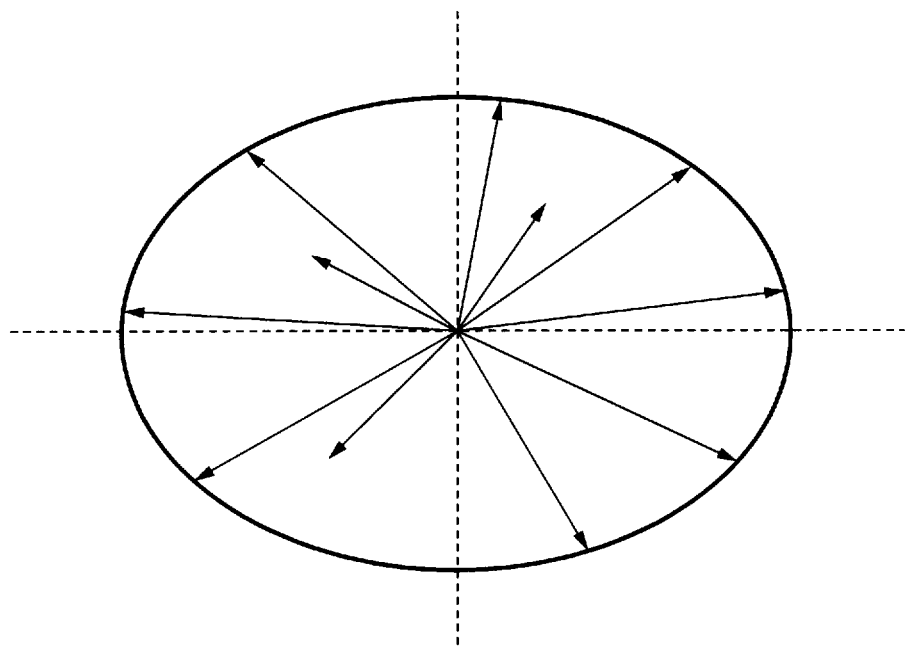

Examples of the visual field range calculated in step S5 are illustrated in FIGS. 6A and 6B. In FIG. 6A, an area (sides of a polygon illustrated in FIG. 6A) defined by matching initial points of all a plurality of exogenous SC vectors and connecting final points of all the plurality of exogenous SC vectors to one another is calculated as the visual field range. On the other hand, FIG. 6B illustrates a visual field range obtained by matching initial points of all a plurality of exogenous SC vectors and approximating an ellipse on the basis of coordinates of final points of, among the plurality of exogenous SC vectors, only exogenous SC vectors larger than a certain value such that all the plurality of exogenous SC vectors are included. As a method for approximating an ellipse on the basis of coordinates of final points of exogenous SC vectors, a common method such as a method of least squares may be used.

In step S6, the visual field range recording unit 140 records the visual field range calculated in the above-described manner. The visual field range is used, for example, for the oversight determination, which will be described later.

In step S7, the visual field range calculation unit 133 does not calculate the visual field range. The visual field range recording unit 140, therefore, does not record the visual field range. In this case, in the oversight determination, which will be described later, a visual field range that has already been recorded by the visual field range recording unit 140 is used.

Operation for Determining Oversight

Figure 7:
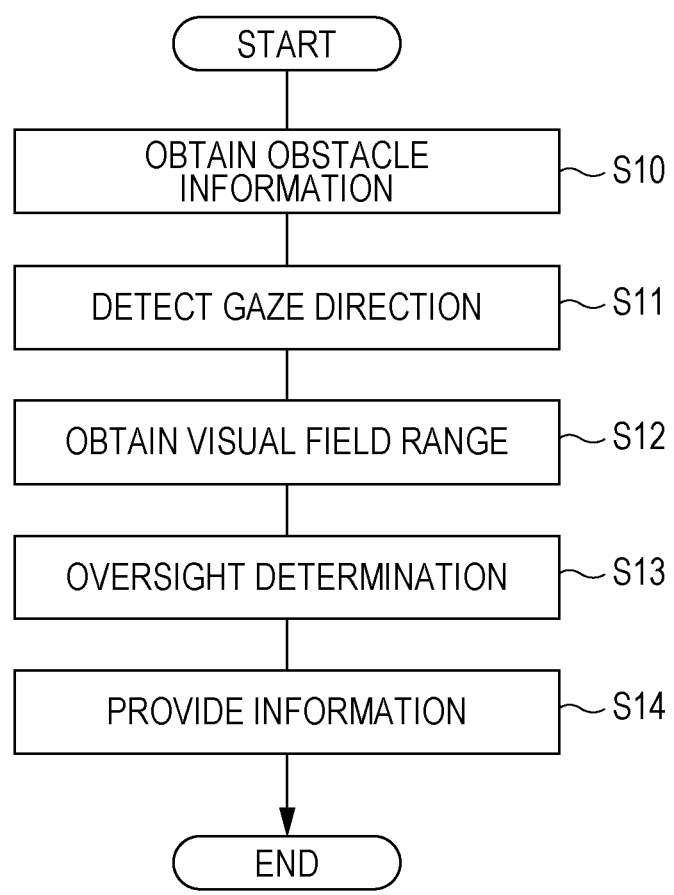
FIG. 7 is a flowchart illustrating an example of an operation for determining an oversight according to the first embodiment of the present disclosure.

Next, an example of the operation for determining an oversight will be described using a flowchart of FIG. 7. The operation for determining an oversight is performed by the oversight determination unit 150. In addition, it is assumed that the operation for determining an oversight is performed independently of the above-described operation for calculating the visual field at certain time intervals T2 such as 10 msec, 20 msec, or 30 msec.

In step S10, the information obtaining unit 110 obtains obstacle information. As described above, the obstacle information is information including presence or absence of an obstacle around the vehicle, the position of the obstacle, the speed of the obstacle relative to the vehicle, and the like. The information obtaining unit 110 outputs the obtained obstacle information to the oversight determination unit 150.

In step S11, the gaze direction detection unit 120 detects the gaze direction of the user. As described above, the gaze direction indicates a direction in which the user gazes and is expressed, for example, by an angle in the horizontal direction and an angle in the vertical direction relative to an origin direction, which is the forward direction of the vehicle. The gaze direction detection unit 120 outputs gaze direction information indicating the detected gaze direction to the oversight determination unit 150. It is to be noted that the origin direction is not limited to the forward direction of the vehicle, and may be an arbitrary direction.

In step S12, the oversight determination unit 150 obtains the visual field range from the visual field range recording unit 140.

In step S13, the oversight determination unit 150 makes an oversight determination, by which it is determined whether the user is missing an obstacle, on the basis of the obstacle information, the gaze direction information, and the visual field range.

Figure 8A:
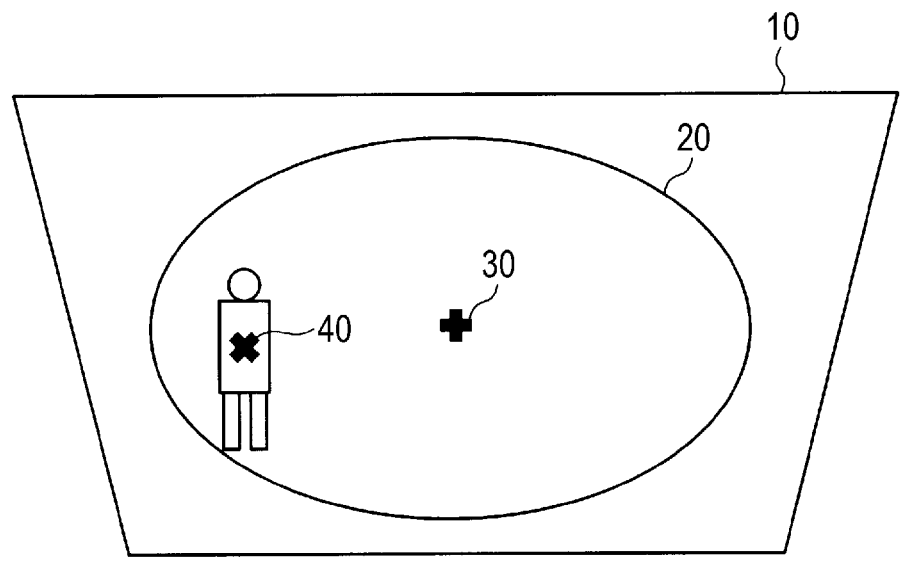
FIGS. 8A and 8B are conceptual diagrams illustrating examples of a result of the operation for determining an oversight according to the first embodiment of the present disclosure.
Figure 8B:
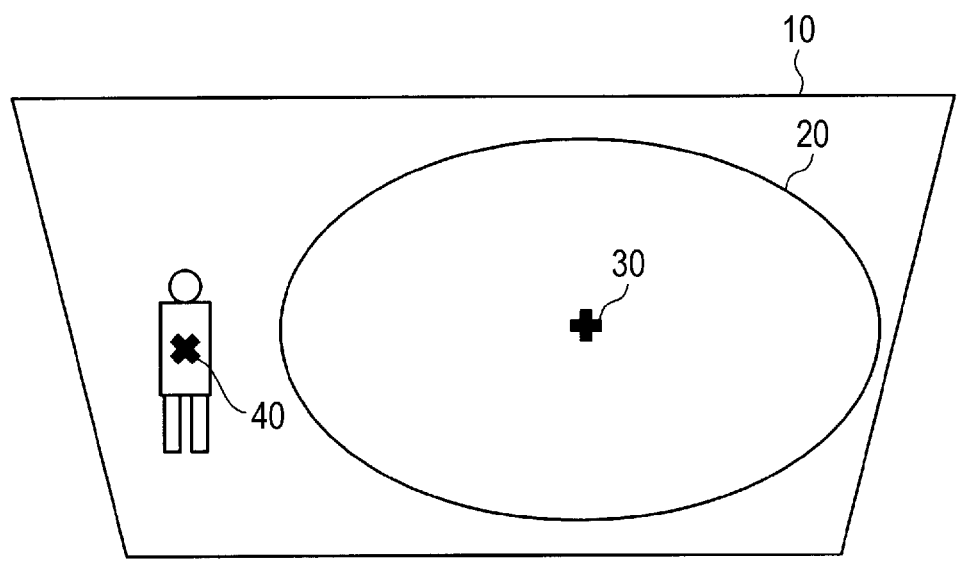

Now, the process for determining an oversight performed in step S13 will be described using FIGS. 8A and 8B. FIGS. 8A and 8B are conceptual diagrams illustrating an oversight determination made when a pedestrian (an example of an obstacle) has been detected in front of a moving vehicle. In FIG. 8A, in a windshield 10 of the vehicle, center coordinates 40 of the obstacle (pedestrian) are included in a visual field range 20 whose center is a gaze point 30. In this case, the oversight determination unit 150 determines that the user is not missing the obstacle (there is no oversight). On the other hand, in FIG. 8B, the center coordinates 40 of the obstacle (pedestrian) are not included in the visual field range 20 whose center is the gaze point 30. In this case, the oversight determination unit 150 determines that the user is missing the obstacle (there is an oversight). If there is an oversight, the oversight determination unit 150 outputs oversight occurrence information indicating that there is an oversight to the display unit 160.

It is to be noted that although the visual field range 20, the gaze point 30, and the center coordinates 40 of the obstacle are included in the range of the windshield 10 in FIGS. 8A and B for the sake of convenience, the visual field range 20, the gaze point 30, and the center coordinates 40 of the obstacle are not displayed on the windshield 40 in practice. That is, the user does not recognize the visual field range 20, the gaze point 30, or the center coordinates 40 of the obstacle.

In step S14, the display unit 160 provides information (e.g., an icon indicating the obstacle or the like) for notifying the user of the oversight on the basis of the oversight occurrence information. It is to be noted that the information may be provided as an alarm sound or a warning along with displayed information.

As described above, the visual field calculation apparatus 130 according to the present embodiment is characterized in that the visual field calculation apparatus 130 detects a saccade on the basis of the gaze direction of the user and calculates the visual field range on the basis of the detected saccade. Because of this characteristic, the visual field calculation apparatus 130 can calculate the visual field range without using a component that provides targets or information obtained by means (e.g., a camera) for detecting a moving object outside the vehicle. The visual field calculation apparatus 130 according to the present embodiment can therefore calculate the visual field range with a simpler configuration.

In addition, in the method of Japanese Unexamined Patent Application Publication No. 2011-206072, for example, if the user arbitrarily gazes at a moving object outside the visual field range or the user gazes at a moving object outside the visual field range for safety purposes, the calculation of the visual field range becomes inaccurate, which is undesirable. On the other hand, the visual field calculation apparatus 130 according to the present embodiment is characterized in that the visual field calculation apparatus 130 calculates the visual field range only on the basis of exogenous SCs while excluding endogenous SCs, which are caused for arbitrariness or safety purposes, from detected saccades. Because of this characteristic, the visual field calculation apparatus 130 can calculate the visual field range more accurately.

In addition, as described in Japanese Unexamined Patent Application Publication No. 2005-95572, for example, a technique for calculating a visual field of a user on the basis of a gaze point of the user and presence or absence of blinks is known. Because the frequency of blinks significantly differs depending on the vigilance of the user or between individuals, however, it is difficult to calculate the visual field range if the vigilance of the user is low or in the case of a user who scarcely blinks. On the other hand, since the visual field calculation apparatus 130 according to the present embodiment detects a saccade on the basis of the gaze direction of the user and calculates the visual field range on the basis of the detected saccade, the visual field calculation apparatus 130 can calculate the visual field range even if the frequency of blinks is low.

In addition, since the driving support system 100 according to the present embodiment detects the user's oversights on the basis of accurately calculated visual field ranges, it is possible to make the user notice the existence of missed obstacles.

It is to be noted that a camera that captures images of a face and an eyeball of the user has been used for describing the gaze direction detection unit 120 in the present embodiment, the gaze direction may be calculated using electrooculography (EOG), instead. The EOG is a method for measuring an eye movement on the basis of a change in the potential of electrodes provided to the left and right of an eyeball or above and below an eyeball. In the EOG, a characteristic of a cornea of an eyeball that the cornea becomes positively charged relative to a retina is used. Because of this characteristic, an eye movement can be measured on the basis of a change in the potential of the electrodes provided to the left and right of the eyeball or above and below the eyeball. When the EOG is used, the gaze direction detection unit 120 as a head-mounted device may measure an eye movement, or electrodes embedded in a seat (mainly a headrest) in the vehicle may come into contact with a head of a seated driver and measure an eye movement.

In addition, although information is provided using the visual field range calculated by the visual field calculation apparatus 130 if the user is missing an obstacle in the description of the present embodiment, control may be performed such that headlight is radiated onto the missed obstacle from the vehicle instead of, or along with, the provision of information. As a result, the user can immediately notice the missed obstacle. A collision between the missed obstacle and the vehicle may be avoided by controlling an accelerator and a steering wheel instead of, or along with, radiating the headlight.

In addition, the saccade detection unit 131 may calculate a saccade displacement SD_XY on a two-dimensional plane in accordance with the following expression (1) on the basis of a saccade displacement ΔX in the horizontal direction and a saccade displacement ΔY in the vertical direction and extract SD_XY that exceeds a certain threshold as an exogenous SC.

$$SD\_XY = \sqrt{(\Delta X^2 + \Delta Y^2)} \quad (1)$$

In addition, although the gaze direction of the user is expressed by an angle (unit: degrees) in the horizontal direction and the vertical direction relative to the origin direction, which is the forward direction of the vehicle, in the description of the present embodiment, the gaze direction of the user is not limited to this. The gaze direction of the user may be expressed, for example, by gaze point coordinates (unit: cm or m) in the horizontal direction and the vertical direction while defining an intersection between a certain vertical plane relative to an origin existing in the forward direction of the vehicle and each gaze direction as a gaze point.

In addition, although an example in which an ellipse is approximated has been described in the present embodiment, the visual field range calculation unit 133 may hold a visual field mode (e.g., a circle, an ellipse, or the like) in advance, for example, and estimate the visual field range on the basis of at least one exogenous SC vector and the visual field model. It is to be noted that the visual field calculation apparatus 130 may include a "visual field model holding unit" that stores and holds the visual field model separately from the visual field range calculation unit 133. This example will be described hereinafter.

Figure 9:
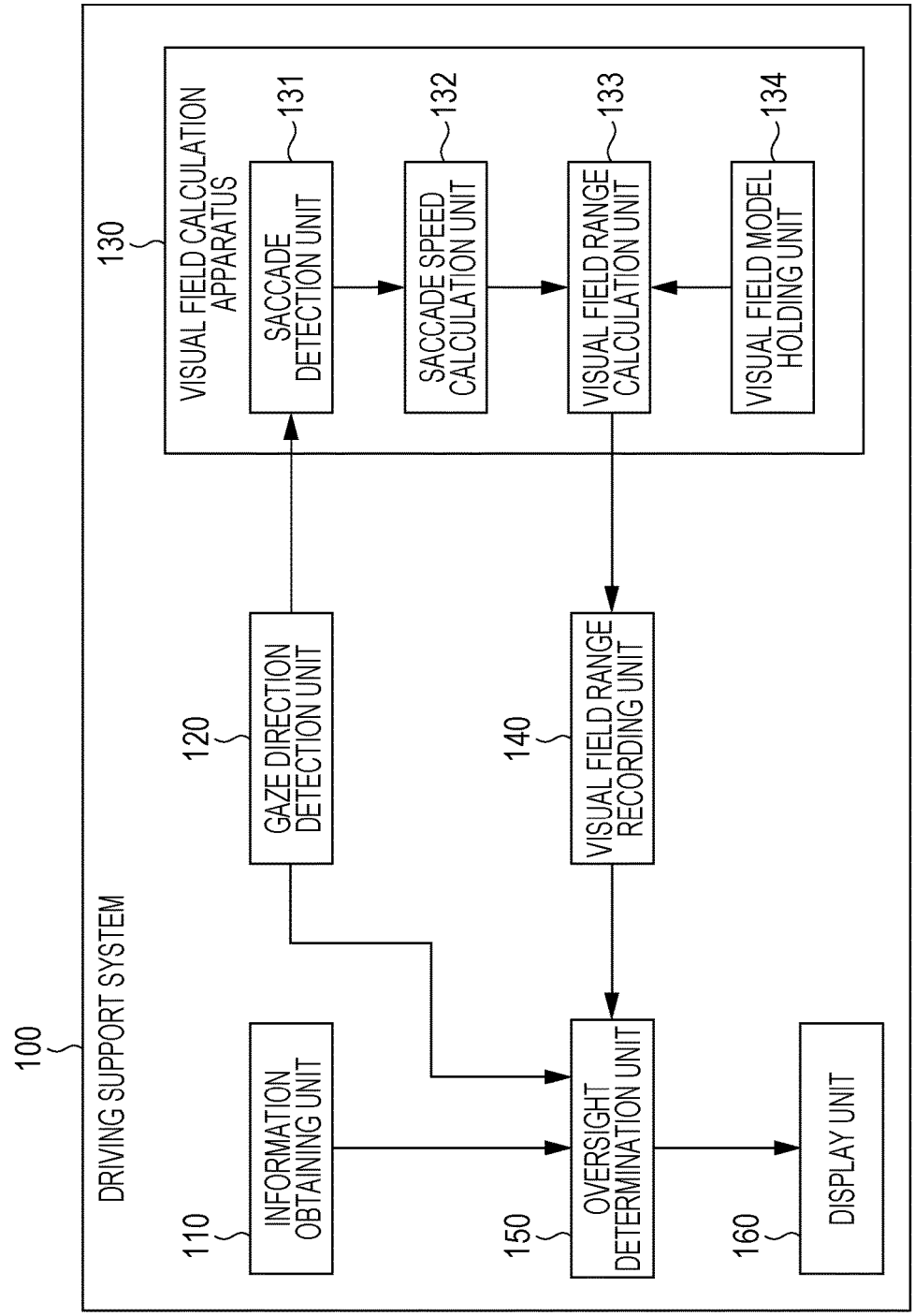
FIG. 9 is a block diagram illustrating an example of the configuration of a driving support system and a visual field calculation apparatus according to a modification of the first embodiment of the present disclosure.

FIG. 9 is a block diagram illustrating an example of the configuration of a driving support system 100 including a visual field calculation apparatus 130 according to a modification of the present embodiment. The configuration illustrated in FIG. 9 is different from the configuration illustrated in FIG. 2 in that the visual field calculation apparatus 130 includes a visual field model holding unit 134. In FIG. 9, the same components as those illustrated in FIG. 2 are given the same reference numerals. In the following description, only differences from the configuration illustrated in FIG. 2 will be described.

Figure 10A:
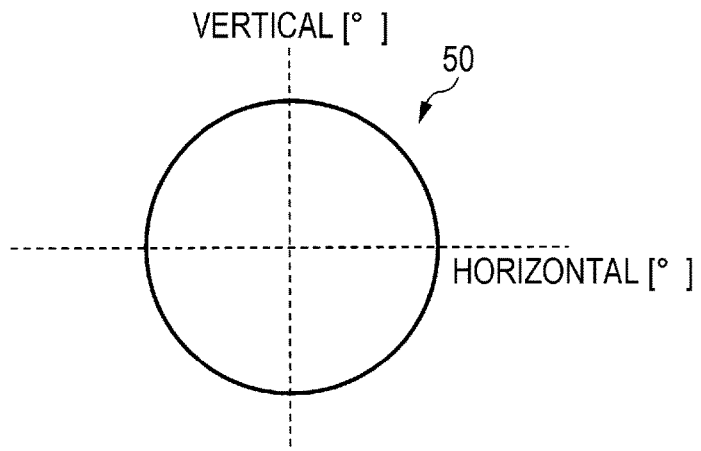
FIGS. 10A to 10C are conceptual diagrams illustrating examples of a visual field pattern according to the modification of the first embodiment of the present disclosure.
Figure 10B:
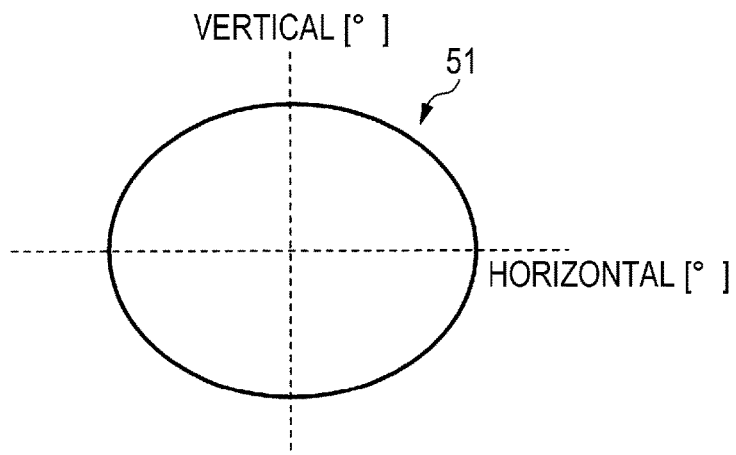
Figure 10C:
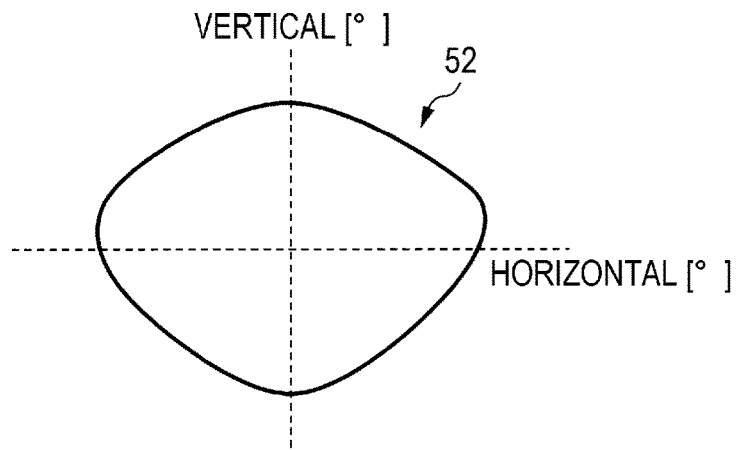

The visual field model holding unit 134 stores at least one visual field model having a certain shape in which a reference point is defined. The visual field model is model data indicating the visual field range of the user. Examples of the visual field model are illustrated in FIGS. 10A to 10C. FIGS. 10A to 10C illustrate three types of visual field models 50, 51, and 52 as examples. The visual field model 50 is a circle whose center is the reference point. The visual field model 51 is an ellipse whose center is the reference point and for which a ratio of a major axis to a minor axis is set to a certain value. In addition, the visual field model 52 has an arbitrary shape in which the reference point is defined.

Operation for Calculating Visual Field

Next, an example of the operation for calculating the visual field will be described using a flowchart of FIG. 11. The operation for calculating the visual field is performed by the visual field calculation apparatus 130. In addition, it is assumed the operation for calculating the visual field is performed independently of the above-described operation for determining an oversight at the certain time intervals T1 such as, for example, 10 minutes, 30 minutes, or 60 minutes. A flow illustrated in FIG. 11 is different from the flow illustrated in FIG. 3 in that steps S21 and S22 are included. In FIG. 11, the same processes as those illustrated in FIG. 3 are given the same reference numerals. Only differences from the flow illustrated in FIG. 3 will be described hereinafter.

In step S21, the visual field range calculation unit 133 obtains the visual field mode held by the visual field model holding unit 134.

In step S22, the visual field range calculation unit 133 calculates the visual field on the basis of a displacement vector of the extracted exogenous SC and the obtained visual field model. The visual field range calculation unit 133 calculates the visual field range by, for example, matching an initial point of the displacement vector of at least one exogenous SC and the reference point of the visual field model and enlarging or reducing a contour of the visual field model in accordance with a final point of the displacement vector.

Figure 12A:
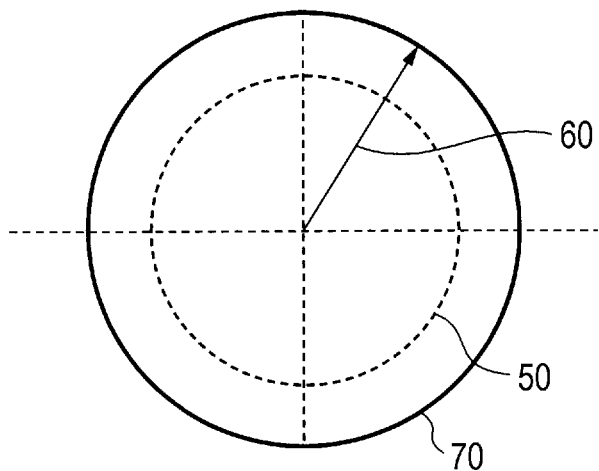
FIGS. 12A to 12C are conceptual diagrams illustrating examples of the operation for calculating the visual field according to the modification of the first embodiment of the present disclosure.
Figure 12B:
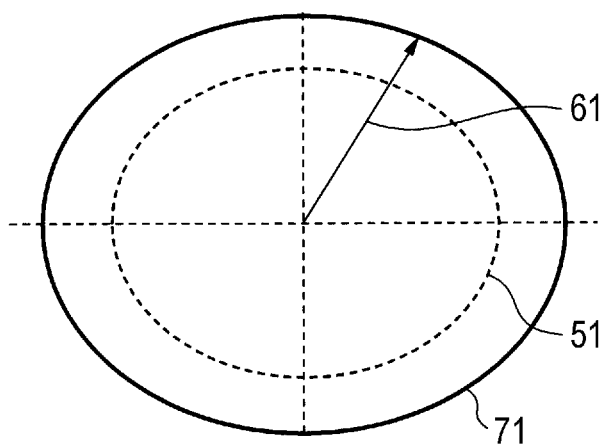
Figure 12C:
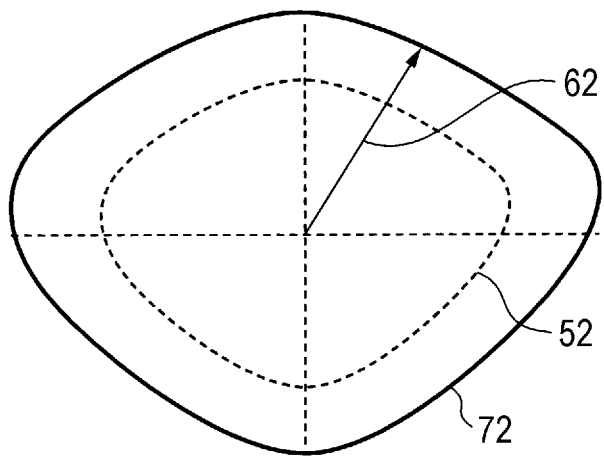

Now, examples of the calculation of the visual field range performed in step S22 will be described with reference to FIGS. 12A to 12C. In FIG. 12A, the visual field range calculation unit 133 enlarges a contour of the visual field model 50 in accordance with a final point of a displacement vector 60 of an exogenous SC. As a result, a visual field range 70 is calculated. In addition, in FIG. 12B, the visual field range calculation unit 133 enlarges a contour of the visual field model 51 in accordance with a final point of a displacement vector 61 of an exogenous SC. As a result, a visual field range 71 is calculated. In addition, in FIG. 12C, the visual field range calculation unit 133 enlarges a contour of a visual field model 52 in accordance with a final point of a displacement vector 62 of an exogenous SC. As a result, a visual field range 72 is calculated.

A visual field range calculated in this manner is recorded in the visual field range recording unit 140 and used for, for example, the above-described oversight determination.

The above-described visual field calculation apparatus 130 according to the modification of the present embodiment can produce the same advantageous effects as the configuration illustrated in FIG. 2. Furthermore, if a displacement vector of at least one exogenous SC can be detected, the visual field calculation apparatus 130 according to the modification of the present embodiment can accurately calculate the visual field range by calculating the visual field range of the user using a predetermined visual field model even when the number of saccades detected in the saccade detection period T3 is small. In addition, since the visual field range can be calculated from a small number of saccades, the visual field calculation apparatus 130 can reduce the certain time intervals T1 (e.g., 10 minutes, 30 minutes, 60 minutes, or the like), which are intervals at which the visual field range is updated. As a result, even if the visual field range has varied due to the complexity of a driving environment during driving, driving speed, or the like, the visual field calculation apparatus 130 can detect a change in the visual field range of the user without delay.

Second Embodiment

The second embodiment of the present disclosure will be described.

Figure 13:
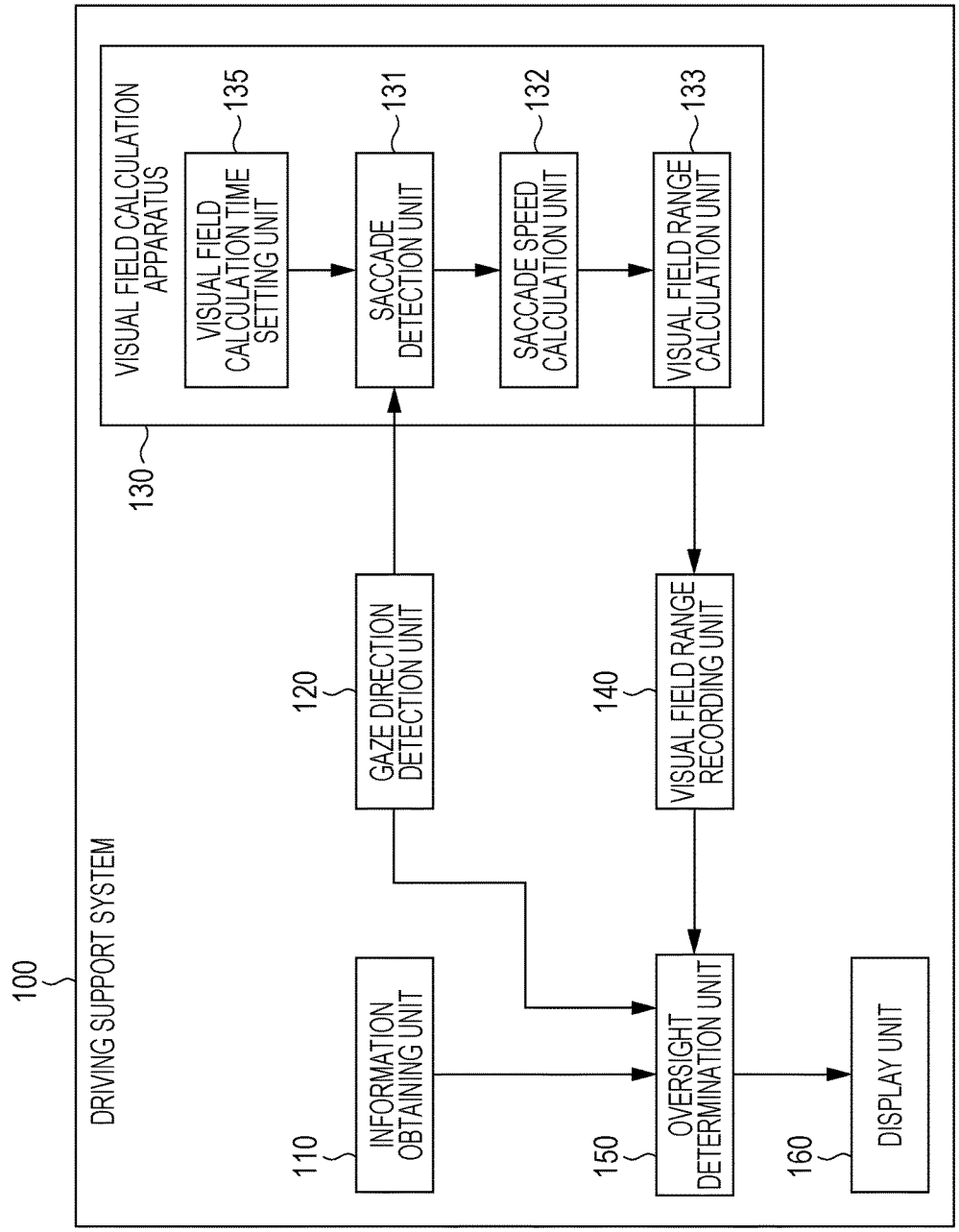
FIG. 13 is a block diagram illustrating an example of the configuration of a driving support system and a visual field calculation apparatus according to a second embodiment of the present disclosure.

FIG. 13 is a block diagram illustrating an example of the configuration of a driving support system 100 including a visual field calculation apparatus 130 according to the present embodiment. The configuration illustrated in FIG. 13 is different from the configuration according to the first embodiment (FIG. 2) in that the visual field calculation apparatus 130 includes a visual field calculation time setting unit 135. In FIG. 13, the same components as those illustrated in FIG. 2 are given the same reference numerals. Only differences from the configuration illustrated in FIG. 1 will be described hereinafter.

The visual field calculation time setting unit 135 sets the saccade detection period T3 as a time used for calculating the visual field by estimating a point in time when the visual field range is assumed to have changed.

Operation for Calculating Visual Field

Figure 14:
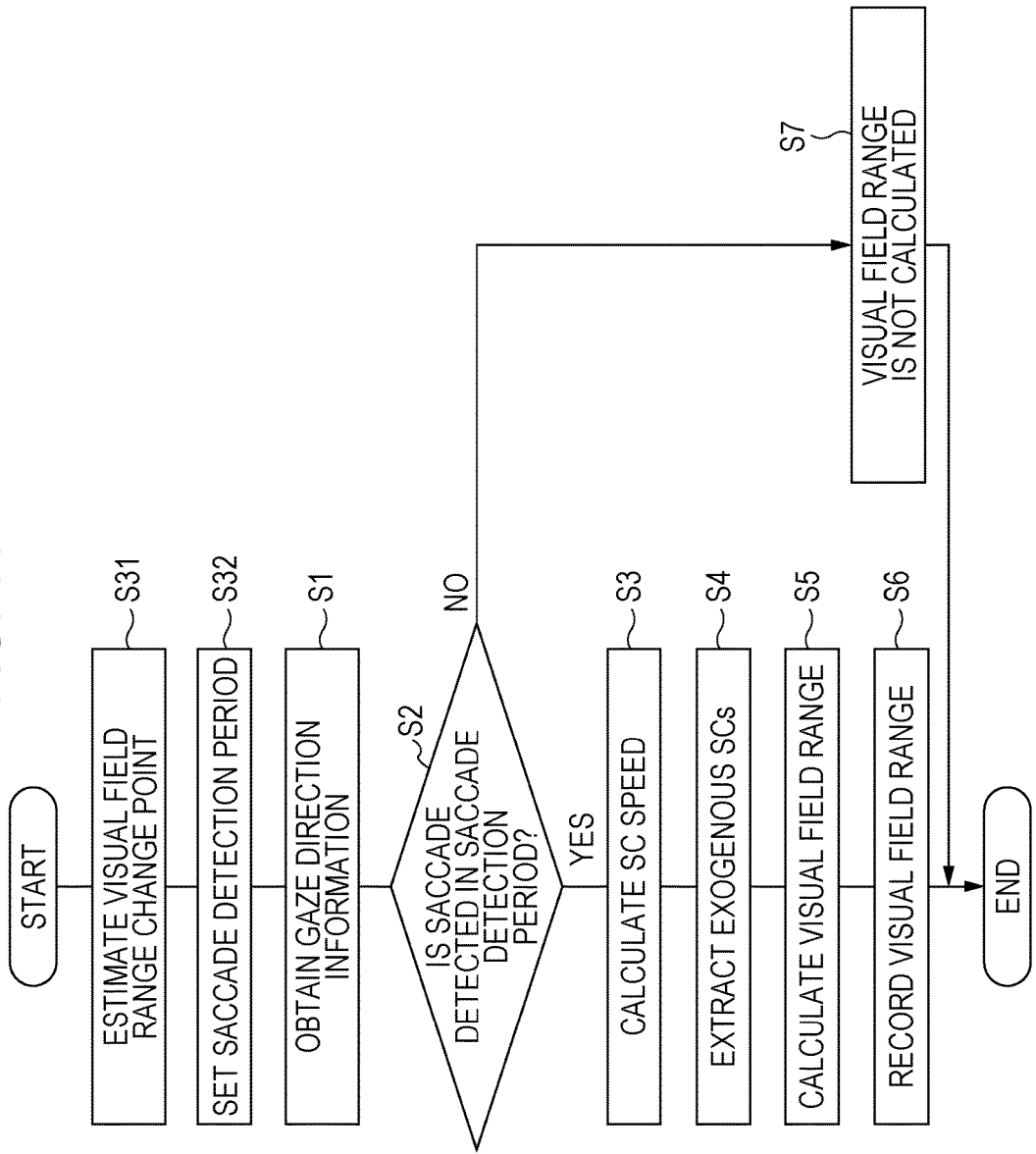
FIG. 14 is a flowchart illustrating an example of an operation for calculating the visual field according to the second embodiment of the present disclosure.

Next, an example of the operation for calculating the visual field will be described using a flowchart of FIG. 14. The operation for calculating the visual field is performed by the visual field calculation apparatus 130. In addition, the operation for calculating the visual field is performed independently of the above-described operation for determining an oversight at the certain time intervals T1 such as, for example, 10 minutes, 30 minutes, or 60 minutes. A flow illustrated in FIG. 14 is different from the flow according to the first embodiment (FIG. 3) in that steps S31 and S32 are included. In FIG. 14, the same processes as those illustrated in FIG. 3 are given the same reference numerals. Only differences from the flow according to the first embodiment will be described hereinafter.

In step S31, after the visual field calculation apparatus 130 starts the operation for calculating the visual field, the visual field calculation time setting unit 135 estimates a point in time (hereinafter referred to as a "visual field range change point") when the visual field range is assumed to have changed before a visual field calculation operation start point. In the estimation of the visual field range change point, information indicating changes in the speed of the vehicle, information for a car navigation system (e.g., information indicating types of roads and information indicating buildings around the roads), and information indicating the vigilance of the user or a distracted state. It is to be noted that details of the estimation will be described using FIG. 15.

In step S32, the visual field calculation time setting unit 135 sets a period (time) between the visual field range change point and the visual field calculation operation start point as a new saccade detection period T3 (S32).

In general, the visual field range of the user during driving dynamically changes depending on the complexity of the driving environment (the number of objects to be paid attention to around the vehicle), the driving speed of the vehicle, the vigilance of the user, the distracted state, and the like. More specifically, it is known that as the driving environment becomes more complex (the number of objects around the vehicle increases), the visual field range of the user becomes narrower, and as the driving speed increases, the visual field range becomes wider. In addition, if the user becomes sleepy and the vigilance of the user decreases during driving, or if the user enters the distracted state as a result of occurrence of a driver distraction such as a concern or a conversation with a fellow passenger, the visual field range tends to be narrower.

Figure 15:
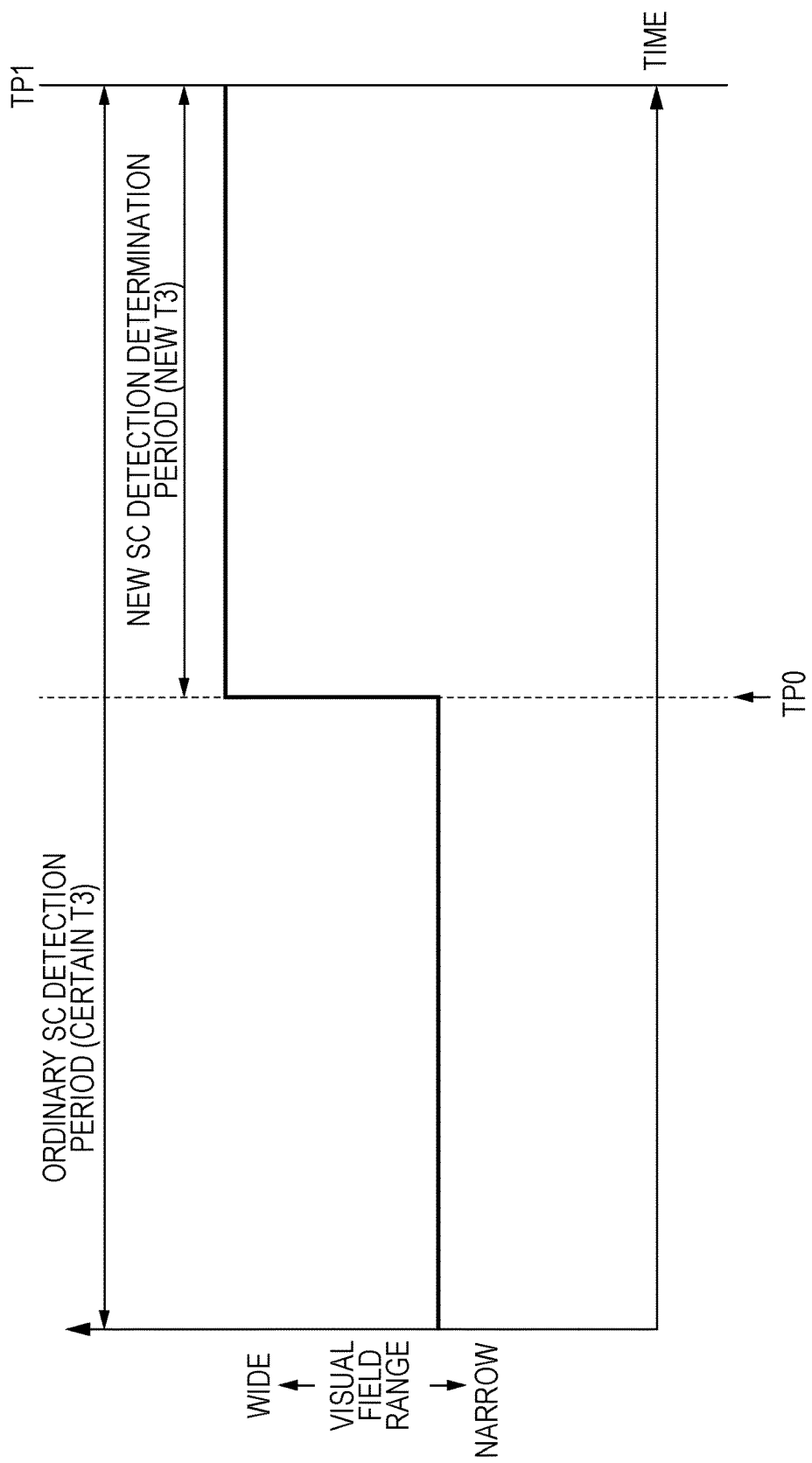
FIG. 15 is a diagram illustrating an example of a change in a visual field range according to the second embodiment of the present disclosure.

FIG. 15 focuses upon a relationship between the driving speed of the vehicle and the visual field range and schematically illustrates a change in the visual field range at a time when general road driving (driving at low to medium speed) changes to highway driving (driving at high speed). Steps S31 and S32 described above will be described with reference to FIG. 15. The visual field calculation time setting unit 135 estimates a point in time when the visual field range has become wider (a point in time when the vehicle has entered a highway from a general road) before a visual field calculation operation start point TP1 as a visual field range change point TP0 (step S31). The visual field calculation time setting unit 135 then sets a period from the visual field range change point TP0 to the visual field range calculation operation start point TP1 as a new saccade detection period T3 (step S32).

The above-described visual field calculation apparatus 130 according to the present embodiment can produce the same advantageous effects as in the first embodiment. Furthermore, if a visual field range change point is detected, the visual field calculation apparatus 130 according to the present embodiment switches to a new saccade detection period T3 using the point as a start point, even if another saccade detection period T3 is set in advance. The visual field calculation apparatus 130 can therefore calculate the visual field range of the user more accurately.

Third Embodiment

The third embodiment of the present disclosure will be described.

Figure 16:
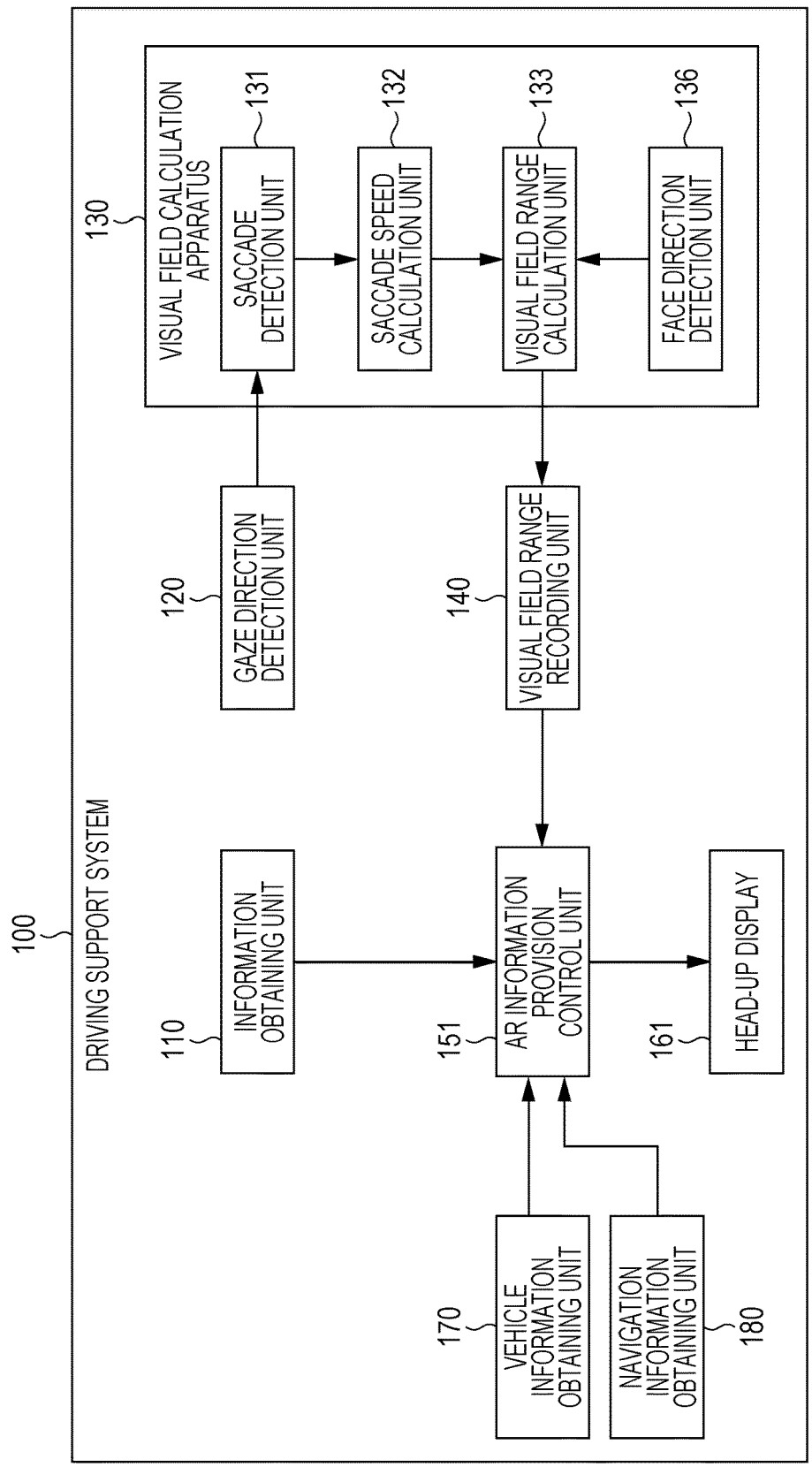
FIG. 16 is a block diagram illustrating an example of the configuration of a driving support system and a visual field calculation apparatus according to a third embodiment of the present disclosure.

FIG. 16 is a block diagram illustrating an example of the configuration of a driving support system 100 including a visual field calculation apparatus 130 according to the present embodiment. The configuration illustrated in FIG. 16 is different from the configuration according to the first embodiment (FIG. 2) in that the visual field calculation apparatus 130 includes a face direction detection unit 136 and the driving support system 100 includes a vehicle information obtaining unit 170 and a navigation information obtaining unit 180. In FIG. 16, the same components as those illustrated in FIG. 2 are given the same reference numerals. Only differences from the configuration according to the first embodiment will be described hereinafter.

The driving support system 100 is a system that displays vehicle information and navigation information (both of which will be described later) on a head-up display along with obstacle information while superimposing these pieces of information upon the foreground so that the user can easily understand the information and the information does not bother the user (hereinafter referred to as "AR display"). In the present embodiment, therefore, the driving support system 100 can be considered to be an information providing system that provides various pieces of information for the user.

The driving support system 100 includes the information obtaining unit 110, the gaze direction detection unit 120, the visual field calculation apparatus 130, the visual field range recording unit 140, the vehicle information obtaining unit 170, the navigation information obtaining unit 180, an AR information provision control unit 151, and a head-up display 161. Furthermore, the visual field calculation apparatus 130 includes the face direction detection unit 136 along with the saccade detection unit 131, the saccade speed calculation unit 132, and the visual field range calculation unit 133.

The vehicle information obtaining unit 170 obtains vehicle information. The vehicle information includes information relating to the vehicle such as, for example, the speed of the vehicle, shift lever information, and fuel information.

The navigation information obtaining unit 180 obtains navigation information. The navigation information is information indicating, for example, the position of the vehicle, names of roads, types of roads, names of buildings (institutions, shops, and the like) around the roads, and the like.

The AR information provision control unit 151 controls a method for displaying the obstacle information from the information obtaining unit 110, the vehicle information from the vehicle information obtaining unit 170, and the navigation information from the navigation information obtaining unit 180 in accordance with the visual field range of the user recorded in the visual field range recording unit 140.

The head-up display 161 performs the AR display by superimposing the obstacle information, the vehicle information, and the navigation information upon the foreground in accordance with the display method controlled by the AR information provision control unit 151. The head-up display 161 is, for example, the entirety of the windshield of the vehicle or an area that is part of the windshield. It is to be noted that the head-up display 161 may be a head-up display independent of the windshield, or may be a head-mounted display of a glasses-type worn by the user.

The face direction detection unit 136 is, for example, a device provided around the steering column of the driver's seat and detects the direction of the user's face on the basis of images of the user's face and eyeball. First, for example, the face direction detection unit 136 detects an area of the user's face and an area of the user's eye through pattern matching. Thereafter, the face direction detection unit 136 calculates angles of the direction of the user's face in the vertical direction and the horizontal direction on the basis of the position of the area of the user's eye relative to the area of the user's face and generates face direction information indicating the angles. It is to be noted that a head-mounted measuring device worn by the user may be used as the face direction detection unit 136. In the case of a head-mounted measuring device, the angles of the user's face in the vertical direction and the horizontal direction can be calculated using a gyro sensor incorporated into the measuring device.

Next, an operation for calculating an effective visual field and an operation for controlling information provision will be described in this order as examples of the operation of the driving support system 100. The operation for calculating the effective visual field is an operation for calculating an effective visual field range on the basis of a relationship between the direction of the user's face and the gaze direction at a time when a saccade occurs. The effective visual field range refers to a range in which the user can receive information during driving only by moving his/her eyes without moving his/her face. In addition, the operation for controlling information provision is an operation for displaying information of higher priority (e.g., the obstacle information) in the effective visual field range through AR display and displaying information of lower priority (e.g., the vehicle information and the navigation information) outside the effective visual field range.

Operation for Calculating Effective Visual Field

First, an example of the operation for calculating the effective visual field will be described using a flowchart of FIG. 17. The operation for calculating the effective visual field is performed by the visual field calculation apparatus 130. In addition, it is assumed that the operation for calculating the effective visual field is performed independently of the operation for controlling information provision, which will be described later, at the certain time intervals T1 such as, for example, 10 minutes, 30 minutes, or 60 minutes. A flow illustrated in FIG. 17 is different from the flow according to the first embodiment (FIG. 3) in that steps S41, S42, and S43 are included. In FIG. 17, the same processes as those illustrated in FIG. 3 are given the same reference numerals. Only differences from the flow according to the first embodiment will be described hereinafter.

In step S41, after the visual field calculation apparatus 130 starts the operation for calculating the effective visual field, the face direction detection unit 136 detects angles (an angle in the vertical direction and an angle in the horizontal direction) of the direction of the user's face in a certain saccade detection period T3 to generate face direction information. As described above, the face direction information is information indicating angles of the direction of the user's face in the vertical direction and the horizontal direction. The face direction detection unit 136 outputs the generated face direction information to the visual field range calculation unit 133.

In step S42, the visual field range calculation unit 133 calculates a face direction displacement at a time when the saccade occurs for each detected saccade.

Now, an example of the calculation of the face direction displacement performed in step S42 will be described with reference to FIGS. 18A and 18B. FIG. 18A is a diagram chronologically illustrating changes in the gaze direction of the user in the saccade detection period T3 and is the same diagram as FIG. 4. On the other hand, FIG. 18B is a diagram chronologically illustrating changes in the direction of the user's face in the saccade detection period T3. t, t+1, t+2, and t+3 illustrated in FIG. 18A correspond to t, t+1, t+2, and t+3, respectively illustrated in FIG. 18B. As illustrated in FIG. 18B, the visual field range calculation unit 133 calculates, at each of the saccades SC(1) to SC(N), a difference in the face direction between an SC start point (a point indicated by a solid circle) and an SC end point (a point indicated by a double circle) detected from the gaze direction of the user as a face direction displacement SD(i)_face (unit: degrees).

In step S43, the visual field range calculation unit 133 extracts only exogenous SCs whose face direction displacements SD(i)_face are equal to or smaller than a threshold SD_face_Th (an example of a second threshold) from among the extracted exogenous SCs as saccades in the effective visual field. The threshold SD_face_Th is predetermined for the horizontal direction and the vertical direction like, for example, ±3 degrees in the horizontal direction and ±2 degrees in the vertical direction.

In step S5, the visual field range calculation unit 133 calculates the effective visual field range using only the saccades in the effective visual field. The effective visual field range is then recorded in the visual field range recording unit 140. It is to be noted that a specific example of the effective visual field range calculated here will be described later using FIG. 20.

Operation for Controlling Information Provision

Figure 19:
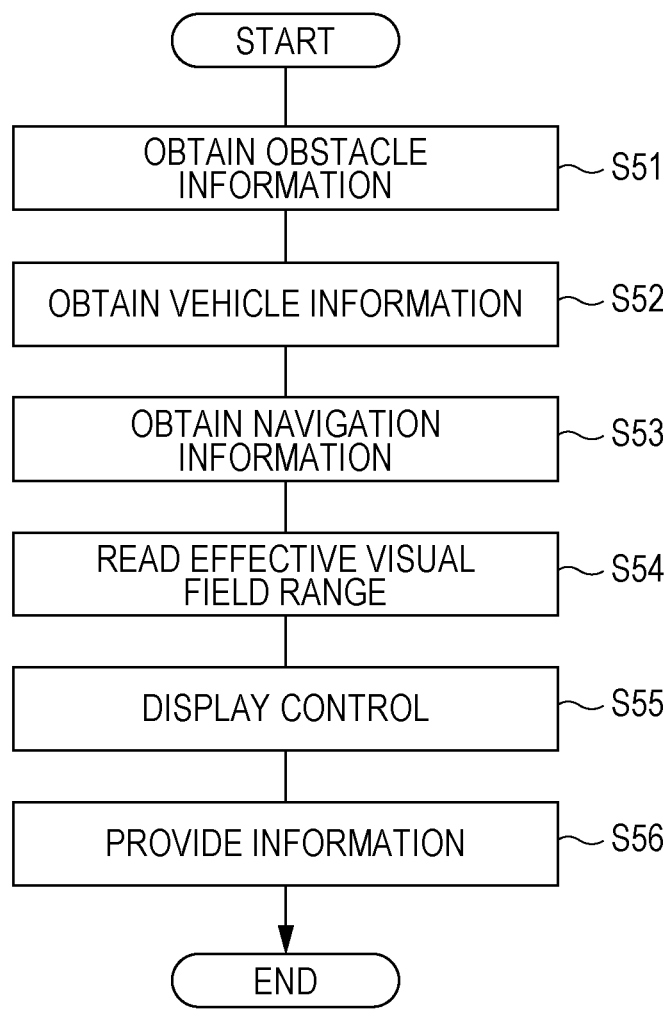
FIG. 19 is a flowchart illustrating an example of an operation for controlling information provision according to the third embodiment of the present disclosure.

Next, an example of the operation for controlling information provision will be described using a flowchart of FIG. 19. The operation for controlling information provision is performed by the visual field calculation apparatus 130. In addition, the operation for controlling information provision is performed independently of the above-described operation for calculating the effective visual field at the certain time intervals T2 such as, for example, 10 msec, 20 msec, or 30 msec.

In step S51, the information obtaining unit 110 obtains obstacle information. As described above, the obstacle information is information including presence or absence of an obstacle around the vehicle, the position of the obstacle, the speed of the obstacle relative to the vehicle, and the like. in addition, in the present embodiment, the information obtaining unit 110 outputs the obtained obstacle information to the AR information provision control unit 151.

In step S52, the vehicle information obtaining unit 170 obtains vehicle information. As described above, the vehicle information is information including, for example, the speed of the vehicle, shift lever information, fuel information, and the like. The vehicle information obtaining unit 170 outputs the obtained vehicle information to the AR information provision control unit 151.

In step S53, the navigation information obtaining unit 180 obtains navigation information. As described above, the navigation information is information including, for example, the position of the vehicle, names of roads, types of roads, names of buildings (institutions, shops, and the like) around the roads, and the like.

In step S54, the AR information provision control unit 151 reads the effective visual field range recorded in the visual field range recording unit 140.

In step S55, the AR information provision control unit 151 controls the display of the head-up display 161 such that the obstacle information, which is of higher priority, is displayed in the read effective visual field range through AR display and the vehicle information and the navigation information, which are of lower priority, are displayed outside the effective visual field range. The priority of the obstacle information, the vehicle information, and the navigation information is assumed to be determined in advance.

In step S56, the head-up display 161 provides information on the basis of the control performed by the AR information provision control unit 151.

Figure 20:
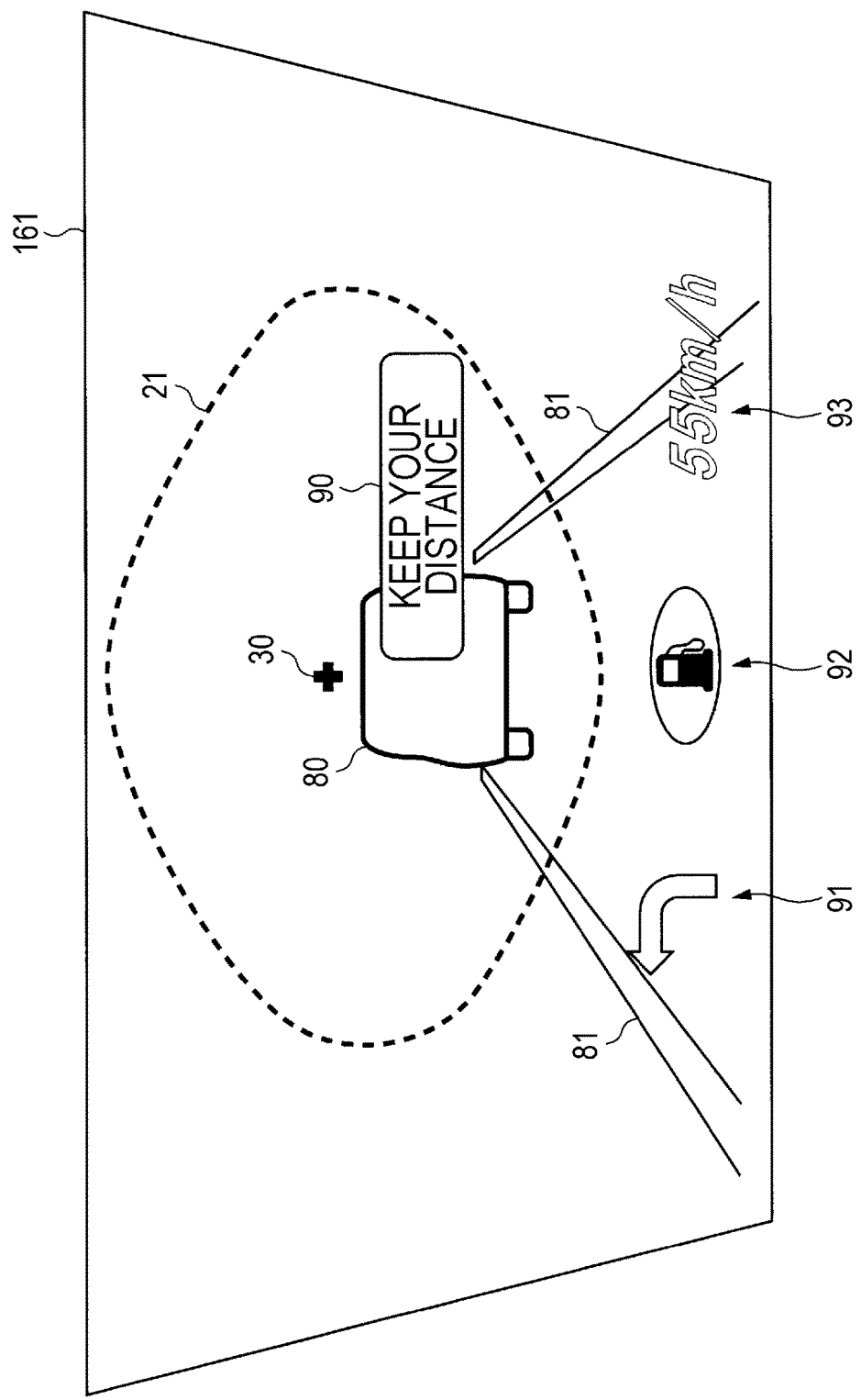
FIG. 20 is a conceptual diagram illustrating an example of augmented reality (AR) display according to the third embodiment of the present disclosure.

Now, an example of the display of the head-up display 161 performed in step S56 will be described. FIG. 20 is a diagram illustrating an example of the information provided on the head-up display 161.

In FIG. 20, a vehicle 80 and lane-dividing lines 81 are actual images. The vehicle 80 is another vehicle running in front of the vehicle and an example of an obstacle indicated by the obstacle information. In addition, in FIG. 20, an effective visual field range 21 exists around a reference point 30 located in front of the user. The effective visual field range 21 is not recognized by the user. A warning message 90 (an example of the obstacle information) that reads "keep your distance" is displayed in the effective visual field range 21 through AR display. On the other hand, an arrow (an example of the navigation information) 91 indicating a traveling direction, an indicator 92 of the remaining amount of fuel, and an indicator 93 (both are examples of the vehicle information) of the speed of the vehicle are displayed outside the effective visual field range 21 at arbitrary positions (e.g., lower portions of the head-up display 161).

It is to be noted that although the reference point 30 is a fixed point located in front of the user as an example in FIG. 20, the gaze direction of the user detected by the gaze direction detection unit 120 may serve as the reference point, instead.

The visual field calculation apparatus 130 according to the present embodiment described above detects a saccade on the basis of the gaze direction of the user and calculates the effective visual field range, in which the user can receive information during driving only by moving his/her eyes without moving his/her face. The visual field calculation apparatus 130 can therefore calculate the effective visual field range without using a component that provides targets or information obtained by means (e.g., a camera) for detecting a moving object outside the vehicle. The visual field calculation apparatus 130 can therefore calculate the visual field range with a simpler configuration. In addition, the effective visual field range can be calculated even if the frequency of blinks is low.

In addition, the visual field calculation apparatus 130 according to the present embodiment can calculate the effective visual field range more accurately by calculating the effective visual field range only on the basis of exogenous SCs.

In addition, the driving support system 100 according to the present embodiment described above displays information of higher priority in the effective visual field range and information of lower priority outside the effective visual field range. As a result, the user can recognize the information of higher priority during driving only by moving his/her eyes without moving his/her face and is not bothered by the displayed information of lower priority. In addition, even if the effective visual field range of the user changes during driving, the driving support system 100 can change the display position of AR display in accordance with the change and can always provide information such that the user can easily understand the information and the information does not bother the user.

It is to be noted that although only the effective visual field range is used for the operation for controlling information provision in the present embodiment, information of lower priority may be displayed outside the effective visual field range but inside the visual field range using the visual field range of the user calculated in the first to third embodiments along with the effective visual field range.

The present disclosure is effective for techniques (e.g., an apparatus, a system, a method, a program, and the like) for calculating the visual field range of the user. It is to be noted that the present disclosure can be applied not only to the user who is driving but also to a technique for calculating the visual field range of the user in situations other than driving using a device that can be worn by the user or the like.

What is claimed is:

1. A visual field calculation apparatus comprising:
a saccade detector that obtains gaze direction information including gaze directions of a user in a saccade detection period, and detects a first plurality of saccades on a basis of a moving amount of each of the gaze directions in unit time;
a saccade speed calculator that calculates a speed of each of the plurality of first saccades in the unit time; and
a visual field range calculator that extracts a second plurality of saccades whose speeds exceed a first threshold from among the first plurality of saccades, calculates displacement vectors of the second plurality of saccades, and calculates an area including an initial point and a final point of each of the displacement vectors as the visual field range of the user,
wherein the first threshold is a value which separates exogenous saccades and endogenous saccades, and
the visual field range of the user is calculated in a range of a surface, and information is displayed on the surface relative to the visual field range.

2. The visual field calculation apparatus according to claim 1, further comprising:
a model holder that holds at least one of visual field models, each visual field model having a predetermined shape,
wherein the visual field range calculator calculates the visual field range of the user by enlarging or reducing one of the at least one visual field models on a basis of the initial point and the final point of each of the displacement vectors.

3. The visual field calculation apparatus according to claim 2,
wherein the predetermined shape s one of a circle, an ellipse for which a ratio of a major axis and a minor axis is set to a certain value, and an arbitrary shape for which a reference point is defined.

4. The visual field calculation apparatus according to claim 1, further comprising:
a visual field calculation time setter that sets a saccade detection period, in which the first plurality of saccades is detected,
wherein the visual field calculation time setter estimates a second point in time when the visual field range of the user has changed before a first point in time when the calculation of the visual field range of the user has started, and
wherein the visual field calculation time setter sets a period from the second point to the first point as the saccade detection period.

5. The visual field calculation apparatus according to claim 1, further comprising:
a face direction detector that detects directions of a face of the user in the saccade detection period,
wherein the visual field range calculator calculates, for each saccade of the first plurality of saccades, a difference in the direction of the face of the user between a point in time when the saccade starts and a point in time when the saccade ends as a face direction displacement,
wherein the visual field range calculator extracts, from among the second plurality of saccades, only a third plurality of saccades in which the face direction displacement is equal to or smaller than a second threshold as saccades in an effective visual field,
wherein the visual field range calculator calculates a displacement vector of each of the third plurality of the saccades in the effective visual field, and
wherein the visual field range calculator calculates, on a basis of each of the displacement vectors, an effective visual field range in which information is able to be received only by moving eyes of the user without moving the face of the user.

6. The visual field calculation apparatus according to claim 5,
wherein the effective visual field range is used as a range in which certain information is subjected to augmented reality display.

7. The visual field calculation apparatus according to claim 1, further comprising:

a determiner that outputs information to a display in response to a determination that the user is missing an obstacle on a basis of a gaze direction of the user and a visual field range of the user.

8. The visual field calculation apparatus according to claim 1, wherein the surface is a windshield.

9. The visual field calculation apparatus according to claim 8, wherein the information is displayed on the surface outside of the visual field range.

10. The visual field calculation apparatus according to claim 9, wherein the information includes at least one of a vehicle speed, shift lever information, fuel information, and a traveling direction.

11. The visual field calculation apparatus according to claim 8, wherein the information is displayed on the surface in the visual field range.

12. The visual field calculation apparatus according to claim 11, wherein the information includes a warning.

13. A method for calculating a visual field, the method comprising:

obtaining gaze direction information including gaze directions of a user in a saccade detection period;

detecting a first plurality of saccades on a basis of a moving amount of each of the gaze directions in unit time;

calculating a speed of each of the plurality of first saccades in the unit time;

extracting a second plurality of saccades whose speeds exceed a first threshold from among the first plurality of saccades;

calculating displacement vectors of the second plurality of saccades; and calculating an area including an initial point and a final point of each of the displacement vectors as a visual field range of the user, wherein the first threshold is a value which separates exogenous saccades and endogenous saccades, and the visual field range of the user is calculated in a range of a surface, and information is displayed on the surface relative to the visual field range.

* * * * *